(12) United States Patent
Gadwood et al.

(10) Patent No.: US 6,441,188 B1
(45) Date of Patent: Aug. 27, 2002

(54) AMINOARYL OXAZOLIDINONE N-OXIDES

(75) Inventors: Robert C. Gadwood, Kalamazoo; Bharat V. Kamdar, Portage, both of MI (US)

(73) Assignee: Pharmacia & Upjohn company, Kalamazoo, MI (US)

( * ) Notice: Subject to any disclaimer, the term of this patent is extended or adjusted under 35 U.S.C. 154(b) by 0 days.

(21) Appl. No.: 09/988,078

(22) Filed: Jun. 28, 2001

Related U.S. Application Data

(62) Division of application No. 08/709,998, filed on Sep. 9, 1996, now Pat. No. 6,277,985.
(60) Provisional application No. 60/003,838, filed on Sep. 15, 1995.

(51) Int. Cl.[7] .............................................. C07D 263/08
(52) U.S. Cl. ...................................... 548/231; 548/232
(58) Field of Search ................................. 548/231, 232

(56) References Cited

U.S. PATENT DOCUMENTS

| 4,722,928 A | 2/1988 | Boswell et al. ............. 514/282 |
| 5,952,324 A | * 9/1999 | Barbachyn et al. ......... 514/211 |

FOREIGN PATENT DOCUMENTS

| WO | WO 95/07271 | * 3/1995 |
| WO | WO 96/13502 | * 5/1996 |
| WO | WO 96/15130 | * 5/1996 |
| WO | WO 96/35691 | * 11/1996 |

OTHER PUBLICATIONS

Chemical Abstracts 118:147332y (1993) Note: Reference is shown incorrectly in the application as 118:147331y.
Cancer and Metastasis Review 12:119–134 (1993).

* cited by examiner

*Primary Examiner*—Brenda Coleman
(74) *Attorney, Agent, or Firm*—Lucy X. Yang

(57) ABSTRACT

The present invention provides for aminoaryl oxazolidinone N-oxide compounds of Formula I

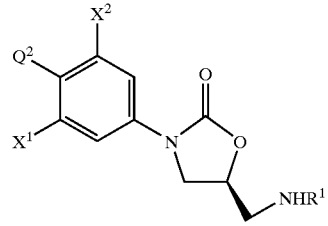

wherein the variables are as defined herein. These compounds are exceedingly water soluble which is useful in preparing pharmaceutical formulations of these compounds. They are also rapidly converted back to the parent amines in vivo, making them useful as prodrugs of the parent amines. They are effective against a number of human and veterinary pathogens, including gram-positive aerobic bacteria such as multiply-resistant staphylococci, streptococci and enterococci as well as anaerobic organisms, such as Bacteroides spp. and Clostridia spp. species, and acid-fast organisms such as *Mycobacterium tuberculosis, Mycobacterium avium* and Mycobacterium spp., and in organisms such as Mycoplasma spp.

5 Claims, No Drawings

AMINOARYL OXAZOLIDINONE N-OXIDES

This application is a divisional application of U.S. patent application Ser. No. 08/709,998, filed on Sep. 9, 1996, now U.S. Pat. No. 6,277,985 which claims the benefit of provisional application U.S. Serial No: 60/003,838, filed Sep. 15, 1995.

FIELD OF THE INVENTION

The present invention provides for aminoaryl oxazolidinone N-oxide compounds. These compounds are exceedingly water soluble which is useful in preparing pharmaceutical formulations of these compounds. They are also rapidly converted back to the parent amines in vivo, making them useful as prodrugs of the parent amines.

These compounds have antibiotic activity comparable to the parent amines. They are effective against a number of human and veterinary pathogens, including gram-positive aerobic bacteria such as multiply-resistant staphylococci, streptococci and enterococci as well as anaerobic organisms, such as Bacteroides spp. and Clostridia spp. species, and acid-fast organisms such as *Mycobacterium tuberculosis, Mycobacterium avium* and Mycobacterium spp., and in organisms such as Mycoplasma spp.

BACKGROUND OF THE INVENTION

A variety of antibiotic oxazolidinone compounds are known in the art. For example, please see the following: WO 95/07271, published Mar. 16, 1995, "Substituted Oxazine and Thiazine Oxazolidinones Antimicrobials"; WO96/15130, published May 23, 1996, "Bicyclic Oxazine and Thiazine Oxazolidinone Antibacterials"; WO96/13502, published May 9, 1996, "Phenyloxazolidinone Antimicrobials"; WO 93/23384, published Nov. 25, 1993, "Oxazolidinone Antimicrobials Containing Substituted Diazine Moieties"; WO 90/02744, published Mar. 22, 1990; U.S. Pat. No. 5,164,510; U.S. Pat. No. 5,225,565; U.S. Pat. No. 5,182,403; "5'-Indolinyl-5β-Amidomethyloxazolidin-2-ones"; WO 95/25106, published Sep. 21, 1995, "Oxazolidinone Derivatives and Pharmaceutical Compositions Containing Them"; WO 93/09103, published May 13, 1993, "Substituted Aryl and Heteroaryl-Phenyloxazolidinones"; WO 95/14684, published Jun. 1, 1995, "Esters of Substituted Hydroxyacetyl-Piperazine Phenyl Oxazolidinones"; PCT/US96/05202, filed Apr. 18, 1996, "Spirocyclic and Bicyclic Diazinyl and Carbazinyl Oxazolidinones"; U.S. Pat. Nos. 5,231,188 and 5,247,090, "Tricyclic [6,6,5]-Fused Oxazolidinone Antibacterial Agents;" WO 96/23788, published Aug. 8, 1996, "Hetero-Aromatic Ring Substituted Phenyloxazolidinone Antimicrobials;" and WO 94/13649, published Jun. 23, 1994, "Tropone-Substituted Phenyloxazolidinone Antibacterial Agents."

Nowhere do these patents, applications or publications teach or suggest N-oxide oxazolidinone compounds.

INFORMATION DISCLOSURE

U.S. Pat. No. 4,722,928 discloses N-oxide prodrug derivatives of 3-hydroxy morphinans and partial morphinans analgesics, agonist-antagonists, and narcotic antagonists, which are useful therapeutic entities providing enhanced bioavailability of these compounds from orally administered dosage forms. In contrast, there is no change in the bioavailability of the N-oxide compounds of the present invention.

This patent further states that there is no way to accurately predict which prodrug structure will be suitable for a particular drug. A derivative which may work well for one drug may not do so for another. Differences in the absorption, metabolism, distribution, and excretion among drugs do not permit generalizations to be made about prodrug design.

Chemical Abstracts 118:147331y (1993) discloses anticancer anthracene amine N-oxide prodrugs with low cytotoxicity which are bioreduced within anaerobic neoplastic tissue to the cytotoxic amine anticancer agents. There is no suggestion that N-oxide prodrugs can be bioreduced in normal tissue. These compounds are also potentially useful against anaerobic bacterial and protozoal infections.

L. H. Patterson, "Rationale for the use of aliphatic N-oxides of cytotoxic anthraquinones as prodrug DNA binding agents: a new class of bioreductive agent," *Cancer and Metastasis Review* 12:119–134 (1993) discloses that such N-oxides are not intrinsically cytotoxic. It further states that investigations into the fate of N-oxide administration to animals show that, in general, aliphatic N-oxides are stable in vivo and are recovered quantitatively following intravenous dosing. Hence, the article concludes that it would appear that aliphatic N-oxides are not metabolised in oxygenated tissue to any significant extent. In contrast, the aliphatic N-oxide compounds of the present invention are surprisingly and unexpectedly reduced back to the parent amine very rapidly in vivo.

The problem in the art is difficulty in formulating the parent amine compounds for intravenous and injectable use. The N-oxide compounds of the present invention have high water solubility and are readily formulated in aqueous vehicles.

SUMMARY OF THE INVENTION

The present invention particularly provides:

A compound of the formula I

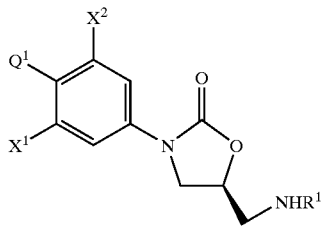

wherein $X^1$ and $X^2$ are independently
—H,
—F, or
—Cl;
wherein $Q^1$ is:

a)

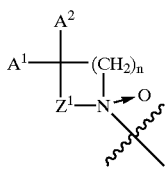

II

-continued b) 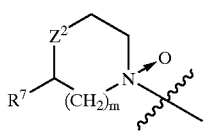

c) 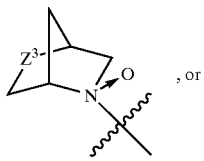, or d) 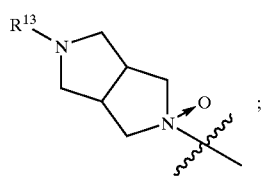;

wherein $Z^1$ is
  a) —$CH_2$—, or
  b) —$CH(R^5)$—$CH_2$—;
wherein $Z^2$ is
  a) —$O_2S$—,
  b) —O—, or
  c) —$N(R^8)$—;
wherein $Z^3$ is
  a) —$O_2S$—, or
  b) —O—;
wherein $A^1$ is
  a) H—, or
  b) $CH_3$—;
wherein $A^2$ is
  a) H—,
  b) HO—,
  c) $CH_3CO_2$—,
  d) $CH_3$—,
  e) $CH_3O$—,
  f) $R^2O$—$CH_2$—C(O)—NH—,
  g) $R^3O$—C(O)—NH—,
  h) $R^4$—C(O)—NH—,
  i) ($C_1$–$C_2$)alkyl—O—C(O)—, or
  j) HO—$CH_2$—; or
$A^1$ and $A^2$ taken together are:

a) 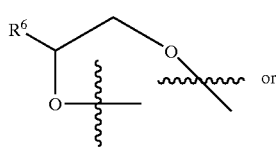 or b) O= wherein $R^1$ is
  a) —CHO,
  b) —$COCH_3$,
  c) —$COCHCl_2$,
  d) —$COCHF_2$,
  e) —$CO_2CH_3$,
  f) —$SO_2CH_3$, or
  g) —$COCH_2OH$;
wherein $R^2$ is
  a) H—,
  b) $CH_3$—,
  c) phenyl-$CH_2$-, or
  d) $CH_3C(O)$—;
wherein $R^3$ is
  a) ($C_1$–$C_3$)alkyl-, or
  b) phenyl-;
wherein $R^4$ is
  a) H—,
  b) ($C_1$–$C_4$)alkyl,
  c) aryl-$(CH_2)p$,
  d) $ClH_2C$—,
  e) $Cl_2HC$—,
  f) $FH_2C$—,
  g) $F_2HC$—, or
  h) ($C_3$–$C_6$)cycloalkyl;
wherein $R^5$ is
  a) H—, or
  b) ($C_1$–$C_3$)alkyl;
wherein $R^6$ is
  a) H—, or
  b) $HOH_2C$—;
wherein $R^7$ is
  a) H—, or
  b) $H_3C$—;
wherein $R^8$ is
  a) $R^2O$—$C(R_{10})(R_{11})$—C(O)—,
  b) $R^3O$—C(O)—,
  c) $R^4$—C(O)—, d) 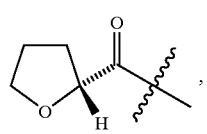, e) 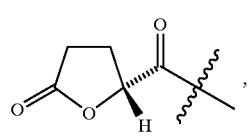, f) $H_3C$—C(O)—$(CH_2)_2$—C(O)—,
g) $R^9$—$SO_2$—, h)

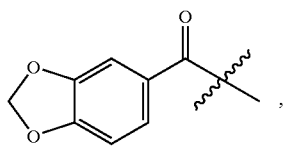
VIII i) $R^{12}$—NH—C(O)—;
wherein $R^9$ is
  a) —$CH_3$,
  b) —$CH_2Cl$
  c) —$CH_2CH$=$CH_2$,
  d) aryl, or
  e) —$CH_2CN$;
wherein $R^{10}$ and $R^{11}$ are independently
  a) H—,
  b) $CH_3$—; or
$R^{10}$ and $R^{11}$ taken together are —$CH_2$—$CH_2$—;
wherein $R^{12}$ is —$(CH_2)_p$-aryl;
wherein $R^{13}$ is
  a) $R^2O$—C($R_{10}$)($R_{11}$)—C(O)—,
  b) $R^3O$—C(O)—,
  c) $R^4$—C(O)—,
  d) $R^9$—$SO_2$—, or
  e) $R^{12}$—NH—C(O)—;
wherein m is zero (0) or one (1);
wherein n is one (1) to three (3), inclusive;
wherein p is zero (0) or one (1);
wherein aryl is phenyl substituted with zero (0) or one (1) of the following:
  a) —F,
  b) —Cl,
  c) —$OCH_3$,
  d) —OH,
  e) —$NH_2$,
  f) —($C_1$-$C_4$)alkyl,
  g) —O—C(O)—$OCH_3$,
  h) —$NO_2$, or
  i) —CN;
with the following provisos:
  1) in the moiety of formula II, $Z^1$ is —CH($R^5$)—$CH_2$— wherein $R^5$ is ($C_1$-$C_3$)alkyl, only when n is one (1), A1 is H and $A^2$ is $R^2O$—$CH_2$—C(O)—NH—, $R^3O$—C(O)—NH—, or $R^4$—C(O)—NH—; and
  2) in the moiety of formula II, when $Z^1$ is —$CH_2$—, n is one (1).

The present invention more particularly provides:
The compound of claim 1 wherein $Q^1$ is the moiety of formula II;
The compound of claim 1 wherein $Q^1$ is the moiety of formula III;
The compound of claim 1 wherein $Q^1$ is the moiety of formula IV;
The compound of claim 1 wherein $Q^1$ is the moiety of formula V;
The compound of claim 1 wherein one of $X^1$ and $X^2$ is —H and the other is —F or wherein $X^1$ is —F and $X^2$ is —F; and
The compound of claim 1 wherein $R^1$ is acetyl.
The compounds of the present invention are named according to the IUPAC or CAS nomenclature system.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, ($C_1$-$C_3$)alkyl refers to alkyl of one to three carbon atoms, inclusive, or methyl, ethyl, propyl and isopropyl, straight and branched forms thereof.

Throughout this application, abbreviations which are well known to one of ordinary skill in the art may be used, such as "Ph" for phenyl, "Me" for methyl, and "Et" for ethyl.

The following Charts I–IX describe the preparation of the parent amine compounds, which are the starting compounds from which the N-oxide compounds of the present invention are prepared. All of the starting compounds are prepared by procedures described in these charts or by procedures analogous thereto, which would be well known to one of ordinary skill in organic chemistry. The following applications and publications which further describe and exemplify these procedures are hereby incorporated by reference herein: WO 95/07271, published Mar. 16, 1995; WO96/15130, published May 23, 1996; WO 95/25106, published Sep. 21, 1995; WO96/13502, published May 9, 1996; WO 93/23384, published Nov. 25, 1993; WO 95/4684, published Jun. 1, 1995; and PCT/US96/05202, filed Apr. 18, 1996.

In the text below corresponding to these charts, the formula at the left margin corresponds to a specific $Q^2$ moiety in the charts and the other variables are as defined with $X^1$ and $X^2$ most often being hydrogen or fluorine and $R^1$ most often being —$COCH_3$, for purposes of example only.

CHART I

I-A Using the procedures from WO 95/07271, published Mar. 16, 1995, page 21, line 33, thru page 23, line 32 for preparation of the intermediate sulfide and then oxidation to the sulfone using the general procedures from WO 95/07271, published Mar. 16, 1995, page 15, line 32 thru page 16, line 14.

I-B Using the procedures described in WO 95/07271, published Mar. 16, 1995, page 21, line 33, thru page 23, line 32, but substituting oxazolidine for thiazolidine.

CHART II

II-A Using the general procedures from WO 95/07271, published Mar. 16, 1995, page 12, line 31, thru page 16, line 14.

II-B Using the general procedures from WO 95/07271, published Mar. 16, 1995, page 12, line 31 thru page 16, line 14, but substituting 2-methylthiomorpholine for thiomorpholine. 2-Methylthiomorpholine is prepared according to the procedure of Gallego, et al, *J. Org. Chem.*, 1993, 58, 3905–11.

II-C Using the general procedures from WO96/15130, published May 23, 1996, Examples 2 and 3 at page 14, line 24, thru page 17, line 21.

CHART III

III-A Using the general procedures from WO 95/07271, published Mar. 16, 1995, page 19, line 6, thru page 21, line 13; and page 23, line 33, thru page 24, line 35.

III-B Using the general procedures from WO96/15130, published May 23, 1996, Example 1 at page 12, line 1, thru page 14, line 22.

CHART IV

IV-A Using the general procedures from WO 95/25106, published Sep. 21, 1995, page 20, line 27 thru page 22, line 5 but substituting azetidine for piperidine.

IV-B Using the general procedures of WO96/13502, published May 9, 1996, Example 11 at page 53, line 32 through page 56, line 3, but substituting 1-(diphenylmethyl)-3-azetidinone in place of 1-benzyl-3-pyrrolidinone. 1-(Diphenylmethyl)-3-azetidinone can be prepared by the procedure of Chatterjee, et al, *Synthesis*, 1973, 153–4.

IV-C From IV-B using the general procedure from WO96/13502, published May 9, 1996, page 56, line 4 through line 17.

IV-D From IV-C using the general procedure from WO 95/25106, published Sep. 21, 1995, page 28, line 26 through page 29, line 5.

IV-E Using the general procedures from WO96/13502, published May 9, 1996, Example 2 at page 33, line 4, thru page 36, line 22.

IV-F Starting with IV-E, and using procedures well known for acetylation; e.g., acetic anhydride and triethylamine in a suitable solvent.

IV-G Using the general procedures from WO96/13502, published May 9, 1996, Example 7 at page 43, line 36, thru page 47, line 28.

IV-H Using the general procedures from WO96/13502, published May 9, 1996, Example 6 at page 40, line 31, thru page 43, line 34.

IV-I Using the procedures of WO96/13502, published May 9, 1996, Example 1 at page 29, line 25 thru page 33, line 2.

IV-J Wherein $R^2$ is H; using the procedure described in WO96/13502, published May 9, 1996, Examples 12 and 13 at page 56, line 19 thru page 59, line 4, but substituting 3-acetylaminoazetidine hydrochloride in place of 3-(trifluoro-acetylamino)pyrrolidine hydrochloride. 3-Acetylaminoazetidine hydrochloride is prepared by the procedure of Nisato, et al., J. Heterocycl. Chem. 1985, 22, 961–3.

IV-J Wherein $R^2$ is methyl; using the procedure described in WO96/13502, published May 9, 1996, Examples 12, 13 and 14 at page 56 line 19 thru page 59 line 27, but substituting 3-acetylaminoazetidine hydrochloride in place of 3-(trifluoroacetylamino)pyrrolidine hydrochloride and substituting methoxyacetyl chloride in place of benzyloxyacetyl chloride.

IV-J Wherein $R^2$ is benzyl; using the procedure described in WO96/13502, published May 9, 1996, Examples 12, 13 and 14 at page 56 line 19 thru page 59 line 27, but substituting 3-acetylaminoazetidine hydrochloride in place of 3-(trifluoroacetylamino)pyrrolidine hydrochloride.

IV-J Wherein $R^2$ is acetyl; using the procedure described in WO96/13502, published May 9, 1996, Examples 12, 13 and 14 at page 56 line 19 thru page 59 line 27, but substituting 3-acetylaminoazetidine hydrochloride in place of 3-(trifluoroacetylamino)pyrrolidine hydrochloride and substituting acetoxyacetyl chloride in place of benzyloxyacetyl chloride.

IV-K Wherein $R^3$ is methyl, ethyl, propyl, or phenyl; using the procedure described in WO96/13502, published May 9, 1996, Examples 12, 13 and 14 at page 56 line 19 thru page 59 line 27, but substituting 3-acetylaminoazetidine hydrochloride in place of 3-(trifluoroacetyl-amino)pyrrolidine hydrochloride and substituting methyl, ethyl, propyl, or phenyl chloroformate in place of benzyloxyacetyl chloride.

IV-L Wherein $R^4$ is hydrogen; using the procedure described in WO96/13502, published May 9, 1996, Examples 12, 13 and 14 at page 56 line 19 thru page 59 line 27, but substituting 3-acetylaminoazetidine hydrochloride in place of 3-(trifluoroacetylamino)pyrrolidine hydrochloride and substituting methyl formate in place of benzyloxyacetyl chloride.

IV-L Wherein $R^4$ is all others listed; using the procedure described in WO96/13502, published May 9, 1996, Examples 12, 13 and 14 at page 56 line 19 thru page 59 line 27, but substituting 3-acetylarninoazetidine hydrochloride in place of 3-(trifluoroacetylamino)pyrrolidine hydrochloride and substituting the appropriate acid chloride in place of benzyloxyacetyl chloride.

IV-M Using the general procedures of WO96/13502, published May 9, 1996, Example 1, Steps 2 thru 7, at page 30, line 14 thru page 33, line 2, but substituting methyl N-benzylazetidine-3-carboxylate in place of 1-(diphenyl-methyl)-3-methoxyazetidine. Methyl N-benzylazetidine-3-carboxylate can be prepared by the procedure of Mason, et al, EP 169602 A1.

IV-N Starting with IV-M and using the general procedures of WO 95/25106, published Sep. 21, 1995, page 22, line 11 through line 20.

CHART V

V-A Using the procedure from WO 95/25106, published Sep. 21, 1995, page 20, Example 1, but using-pyrrolidine instead of piperidine.

V-B Using the procedures of WO96/13502, published May 9, 1996, Example 11 at page 53, line 32, thru page 56, line 3.

V-C From V-B, following the procedure of WO96/13502, published May 9, 1996, page 56, lines 4 through 17.

V-D From V-C, using the general procedure of WO 95/25106, published Sep. 21, 1995, page 28, line 26, thru page 29, line 5.

V-E Using the procedures described in WO96/13502, published May 9, 1996, Example 10 at page 50, line 25, thru page 53, line 30. Or, from V-C by reduction using methods well known in the art such as sodium borohydride in methanol.

V-F From V-E using standard acetylation procedures; e.g., acetic anhydride in pyridine.

V-G As described in WO96/13502, published May 9, 1996, Example 7 at page 43, line 36, thru page 47, line 28 but substituting 1-benzyl-3-methyl-3-pyrrolidinol hydrochloride for 1-(diphenylmethyl)-3-methyl-3-azetidinol hydrochloride. 1-Benzyl-3-methyl-3-pyrrolidinol hydrochloride can be prepared from 1-benzyl-3-pyrrolidinone by methods known in the art, eg, reaction with methylmagnesium bromide and treatment of the product with one equivalent of hydrochloric acid. 1-Benzyl-3-pyrrolidinone is commercially available.

V-H Using the general procedures of WO96/13502, published May 9, 1996, Example 6 at page 40, line 31 through page 43, line 34, but substituting 1-benzyl-3-methyl-3-pyrrolidinol hydrochloride (prepared as described above) in place of 1-(diphenylmethyl)-3-methyl-3-azetidinol hydrochloride.

V-I As described in WO96/13502, published May 9, 1996, Example 1 at page 29, line 25, thru page 33, line 2, but substituting commercially available 1-benzyl-3-pyrrolidinol for 1-(diphenylmethyl)-3-azetidinol.

V-J Wherein $R^2$ is H and $R^5$ is H; using the procedure described in WO96/13502, published May 9, 1996, Examples 12 and 13 at page 56, line 19, thru page 59, line 4;

V-J Wherein $R^2$ is methyl and $R^5$ is H; using the procedure described in WO96/13502, published May 9, 1996, Example 12 at page 56, line 19 thru page 58, line 27 but substituting methoxyacetyl chloride for benzyloxyacetyl chloride.

V-J Wherein $R^2$ is benzyl and $R^5$ is H; using the procedure described in WO96/13502, published May 9, 1996, Example 12 at page 56, line 19 thru page 58, line 27.

V-J Wherein $R^2$ is acetyl and $R^5$ is H; using the procedure described in WO96/13502, published May 9, 1996, Example 12 at page 56, line 19 thru page 58, line 27 but substituting acetoxyacetyl chloride for benzyloxyacetyl chloride.

V-J Where $R^2$ is H and $R^5$ is methyl; using the procedures described in WO96/13502, published May 9, 1996, Example 15 at page 62, lines 5–28.

V-J Wherein $R^2$ is benzyl and $R^5$ is methyl; using the procedures described in WO96/13502, published May 9, 1996, Example 15, Step 1, at page 62, lines 5–19.

V-J Wherein $R^2$ is methyl or acetyl and $R^5$ is methyl; using the procedures described in WO96/13502, published May 9, 1996, Example 15, Step 1, at page 62, lines 5–19, but substituting methoxyacetyl chloride or acetoxyacetyl chloride for benzyloxyacetyl chloride.

V-J Wherein $R^5$ is other alkyl; using the general procedures described above but subsituting other 4-alkyl-3-aminopyrrolidines in place of 3-amino-4-methylpyrrolidine.

V-K Wherein $R^3$ is methyl, ethyl, propyl or phenyl and $R^5$ is H; using the procedure described in WO96/13502, published May 9, 1996, Example 12 at page 56, line 19 thru page 58, line 27 but substituting methyl chloroformate, ethyl choroformate, propylchloroformate, or phenylchloroformate for benzyloxyacetyl chloride.

V-K Wherein $R^3$ is methyl, ethyl, propyl, or phenyl and $R^5$ is methyl; by reaction of (S)-(N)-[[[3-fluoro-4-(3-amino-4-methylpyrrolidinyl)phenyl]-2-oxo-5-oxazolidinyl]methyl]acetamide with the appropriate chloroformate. The above amine is prepared according to the procedures of WO96/13502, published May 9, 1996, Example 14, Steps 1–8, at page 59, line 6 through page 61, line 29.

V-K Wherein $R^5$ is other alkyl; From the appropriate amine and chloroformate.

The amine is prepared according to the procedures of WO96/13502, published May 9, 1996, Example 14, Steps 1–8, at page 59, line 6 through page 61, line 29, but starting with other 3-alkyl-4-aminopyrrolidines in place of 4-amino-3-methylpyrrolidine.

V-L Where $R^4$ is H and $R^5$ is H; using the procedure described in WO96/13502, published May 9, 1996, Example 12 at page 56, line 19 thru page 58, line 27 but substituting methyl formate in place of benzyloxyacetyl chloride.

V-L Where $R^4$ is all others listed and $R^5$ is H; using the procedure described in WO96/13502, published May 9, 1996, Example 12 at page 56, line 19 thru page 58, line 27 but substituting the appropriate acid chloride in place of benzyloxyacetyl chloride.

V-L Where $R^4$ is H and $R^5$ is methyl; by reaction of formic acid and dicyclohexylcarbodiimide. The required amine is prepared according to the procedures of WO96/13502, published May 9, 1996, Example 14, Steps 1–8, at page 59, line 6 through page 61, line 29.

V-L Where $R^4$ is all others and $R^5$ is methyl; by reaction of (S)-(N)-[[[3-fluoro-4-(3-amino-4-methylpyrrolidinyl)phenyl]-2-oxo-5-oxazolidinyl]methyl]acetamide with the appropriate acid chloride. The required amine is prepared according to the procedures of WO96/13502, published May 9, 1996, Example 14, Steps 1–8, at page 59, line 6 through page 61, line 29.

V-L Where $R^5$ is other alkyl; Using the above procedures, but starting with other 3-alkyl-4-aminopyrrolidines in place of 4-amino-3-methylpyrrolidine.

V-M Using the general procedure from WO 95/25106, published Sep. 21, 1995, page 22, lines 6 through 12, 5, but using pyrrolidine-3-carboxylic acid methyl ester instead of piperidine-4-carboxylic acid ethyl ester. Pyrrolidine-3-carboxylic acid methyl ester is prepared by the procedure of Morgans, et al, *Tetrahedron Lett.*, 1979, 1959.

V-N From V-M, using the general procedure of WO 95/25106, published Sep. 21, 1995, page 22, lines 12 through 20.

CHART VI

VI-A Using the general procedures from WO 95/25106, published Sep. 21, 1995, page 20, line 27, thru page 22, line 5.

VI-B Using the procedure of WO 95/25106, published Sep. 21, 1995, WO 95/25106, published Sep. 21, 1995, page 22, line 21 thru line 26.

VI-C From VI-B, using the procedure from WO 95/25106, published Sep. 21, 1995, page 22, lines 27 through 35.

VI-D From VI-C, using the procedure from WO 95/25106, published Sep. 21, 1995, page 28, line 26 thru page 29, line 5.

VI-E Prepared from VI-C by reduction via standard procedures known in the art; eg, sodium borohydride in methanol.

VI-F Prepared from VI-E by procedures known in the art; eg, acetic anhydride and triethylamine.

VI-G Using the procedures from WO96/13502, published May 9, 1996, Example 7, page 43, line 36 thru page 47, line 28 but substituting commercially available 4-hydroxy-4-methylpiperidine for 3-hydroxy-3-methylazetidine.

VI-H Using the procedures from WO 95/25106, published Sep. 21, 1995, page 20, line 27 thru page 22, line 5, but substituting 4-methoxy-4-methylpiperidine in place of piperidine. 4-Methoxy-4-methylpiperidine can be prepared according to the procedure of McManus, et al, *J. Med. Chem.*, 1965, 8, 766–776.

VI-I Using the procedures from WO 95/25106, published Sep. 21, 1995, page 20 line 27 thru page 22, line 5, but substituting 4-methoxypiperidine for piperidine. 4-Methoxypiperidine can be made by the procedure of McManus, et al, *J. Med. Chem.*, 1965, 8, 766–776.

VI-J Wherein $R^2$=H; Prepared by reaction of (S)-N-[[3-[4-(4-aminopiperidinyl)-3-fluorophenyl]-2-oxo-5-oxazolidinyl]methyl]acetamide (prepared according to the procedures of WO 95/25106, published Sep. 21, 1995, page 22, line 36 thru page 23, line 24) with acetoxyacetyl chloride and triethylamine followed by hydrolysis of the acetoxy group with methanolic potassium carbonate.

VI-J Wherein $R^2$=methyl; prepared by reaction of the starting material of VI-J ($R^2$=H) with methoxyacetyl chloride and triethylamine.

VI-J Wherein $R^2$ is benzyl; prepared by reaction of the starting material of VI-J ($R^2$=H) with benzyloxyacetyl chloride and triethylamine.

VI-J Wherein $R^2$ is acetyl; prepared by reaction of the starting material of VI-J ($R^2$=H) with acetoxyacetyl chloride and triethylamine.

VI-K Wherein $R^3$ is methyl, ethyl, propyl, or phenyl; prepared by reaction of the starting material of VI-J ($R^2$=H) with methyl-, ethyl-, propyl-, or phenylchloroformate.

VI-L Wherein R$^4$=H; By reaction of the starting material of VI-J (R$^2$=H) with methylformate.

VI-L Wherein R$^4$=all others listed; By reaction of the starting material of VI-J (R$^2$=H) with the appropriate acid chloride.

VI-M Using the procedure from WO 95/25106, published Sep. 21, 1995, page 22, line 6 thru line 12.

VI-N Using the procedure from WO 95/25106, published Sep. 21, 1995, page 22, lines 12 through 20.

CHART VII

VII-A Using the general procedures of WO 95/25106, published Sep. 21, 1995, page 20, line 27 through page 22, line 5, but substituting commercially available azepine in place of piperidine.

VII-B Using the procedure of WO 95/25106, published Sep. 21, 1995, page 22, line 21 thru line 26 but substituting 1,4-dioxo-8-aza-spiro[4.6]undecane for 1,4-dioxo-8-aza-spiro[4.5]decane. 1,4-Dioxo-8-aza-spiro[4.6]undecane can be prepared by the procedure of R. A. Johnson, et al, *J. Org. Chem.*, 1968, 33, 3187–3195.

VII-C From VII-B, following the procedure of WO96/13502, published May 9, 1996, page 56, lines 4 through 17.

VII-D From VII-C using the general procedure of WO 95/25106, published Sep. 21, 1995, page 28, line 26, thru page 29, line 5.

VII-E Prepared from VII-C by reduction via standard procedures known in the art;
eg, sodium borohydride in methanol.

VII-F Prepared from VII-E by procedures known in the art; eg, acetic anhydride and triethylamine.

VII-G Using the procedures from WO96/13502, published May 9, 1996, Example 7, page 43, line 36 thru page 47, line 28 but substituting 4-hydroxy-4-methyl-azepine for 3-hydroxy-3-methylazetidine. 4-Hydroxy-4-methylazepine can be prepared by the procedure pf Grob, et al, *Helv. Chim.Acta*, 1962, 45, 1823–1830.

VII-H Using the general procedures of WO96/13502, published May 9, 1996, Example 6, page 40, line 31 through page 43, line 34, but substituting 1-benzyl-4-methyl-4-azepinol in place of 1-(diphenylmethyl)-3-methyl-3-azetidinol hydrochloride. 1-Benzyl-4-methyl-4-azepinol can be prepared by the reaction of methyl magnesium bromide with 1-benzyl-4-azepinone. 1-Benzyl-4-azepinone can be prepared by the procedure of Casy, et al, *J. Chem. Soc.* 1964, 5130–5132.

VII-I As described in WO96/13502, published May 9, 1996, Example 1, at page 29, line 25, thru page 33, line 2, but substituting 1-benzyl-4-azepinol for 1-(diphenylmethyl)-3-azetidinol. 1-Benzyl-4-azepinol can be prepared by the procedure of S. Sakanoue, et al, *Chem. Pharm. Bull.*, 1990 38, 2981–2985.

VII-J Wherein R$^2$ is H; using the procedure described in WO96/13502, published May 9, 1996, Examples 12 and 13, page 56, line 19, thru page 59, line 4 but substituting 4-(trifluoroacetylamino)azepine in place of 3-(trifluoroacetylamino)pyrrolidine.
4-(Trifluoroacetylamino)azepine can be prepared by reaction of 1-benzyl-4-azepinamine with trifluoroacetic anhydride in a suitable solvent such as chloroform, followed by removal of the benzyl protecting group via hydrogenolysis using palladium on carbon as a catalyst in a solvent such as ethyl acetate. 1-Benzyl-4-azepinamine can be prepared by the procedure of Morosawa, et al, *Bull. Chem. Soc. Jpn.*, 1958, 31, 418–422.

VII-J Wherein R$^2$ is methyl; using the procedure described in WO96/13502, published May 9, 1996, Example 12, page 56, line 19 through page 58, line 27, but substituting 4-(trifluoroacetylamino)azepine for 4-(trifluoroacetylamino)pyrrolidine and substituting methoxyacetyl chloride in place of benzyloxyacetyl chloride.

VII-J Wherein R$^2$ is benzyl; using the procedure described in WO96/13502, published May 9, 1996, Example 12, page 56, line 19 through page 58, line 27, but substituting 4-(trifluoroacetylamino)azepine for 4-(trifluoroacetylamino)pyrrolidine.

VII-J Wherein R$^2$ is acetyl; using the procedure described in WO96/13502, published May 9, 1996, Example 12, page 56, line 19 through page 58, line 27, but substituting 4-(trifluoroacetylamino)azepine for 4-(trifluoroacetylamino)pyrrolidine and substituting acetoxyacetyl chloride in place of benzyloxyacetyl chloride.

VII-K Wherein R$^3$ is methyl, ethyl, propyl, or phenyl; prepared by reaction of (S)-N-[[3-[4-(4-aminoazepinyl)-3-fluorophenyl]-2-oxo-5-oxazolidinyl]methyl]-acetamide (prepared as an intermediate in the synthesis of VII-J) with the appropriate chloroformate and triethylamine in chloroform.

VII-L Wherein R$^4$ is H; Prepared by reaction of (S)-N-[[3-[4-(4-aminoazepinyl)-3-fluorophenyl]-2-oxo-5-oxazolidinyl]methyl]acetamide (prepared as an intermediate in the synthesis of VII-J) with formic acid according to the general procedure of WO 93/23384, published Nov. 25, 1993, page 23, lines 4–17.

VII-L Wherein R$^4$ is all others; Prepared by reaction of (S)-N-[[3-[4-(4-aminoazepinyl)-3-fluorophenyl]-2-oxo-5-oxazolidinyl]methyl]acetamide (prepared as an intermediate in the synthesis of VII-J) with the appropriate acid chloride and triethylamine.

VIII-M Using the procedure from WO 95/25106, published Sep. 21, 1995, page 22, line 6 thru line 12, but substituting azepine-4-carboxylic acid ethyl ester in place of piperidine-4-carboxylic acid ethyl ester. Azepine-4-carboxylic acid ethyl ester can be prepared from azepine-4-carboxylic acid by normal procedures known in the art, eg, reaction with ethanol and hydrochloric acid. Azepine-4-carboxylic acid can be prepared by the procedure of Krogsgaard-Larsen, et al, Eur. *J. Med. Chem. Chim. Ther.*, 1979, 14, 157–164.

VII-N From VII-M, using the general procedure of WO 95125106, published Sep. 21, 1995, page 22, lines 12 through 20.

CHART VIII

VIII-A Wherein R$^2$=H; According to the procedure of WO 95/14684, published Jun. 1, 1995, page 9, lines 1–28.

VIII-A Wherein R$^2$=methyl; According to the general procedures of WO 93/23384, published Nov. 25, 1993, page 19, lines 26–33.

VIII-A Wherein R$^2$=benzyl; According to the procedure of WO 95/14684, published Jun. 1, 1995, page 9, lines 1–14.

III-A Wherein R$^2$=acetyl; According to the procedure of WO 95/14684, published Jun. 1, 1995, page 28, lines 24–35.

VIII-B Wherein R$^3$=Me, Et, Pr, or Ph; Using the general procedure from WO 93/23384, published Nov. 25, 1993, page 23, lines 19–28 and substituting methyl-, ethyl, propyl, or phenylchloroformate as appropriate.

VIII-C Wherein R$^4$=H; Using the general procedures from WO 93/23384, published Nov. 25, 1993, page 23, lines 4–17.

VIII-C Wherein R$^4$=all others; Using the general procedures from WO 93/23384, published Nov. 25, 1993, page 23, lines 19–28, and substituting the appropriate acid chloride for methylchloroformate.

VIII-D Prepared according to the general procedure found in WO 93/23384, published Nov. 25, 1993, page 25, lines 13–25.

VIII-E Prepared according to the general procedure from WO 93/23384, published Nov. 25, 1993, page 25, lines 13–25, but substituting commercially available 5-oxo-2-tetrahydrofurancarboxylic acid in place of (R)-2-tetrahydrofuranoic acid.

VIII-F Prepared according to the procedure of WO 93/23384, published Nov. 25, 1993, page 18, lines 10–17.

VIII-G Prepared from N-[[3-[4-[3-fluoro-4-(1-piperazinyl)]phenyl]-2-oxo-5-oxazolidinyl]methyl]-acetamide and the appropriate sulfonyl chloride using the general procedure from WO 93/23384, published Nov. 25, 1993, page 23, lines 19–28. Methyl, chloromethyl, allyl, and substituted arylsulfonyl chlorides are commercially available. Cyanomethylsulfonyl chloride can be prepared according to the procedure of M. P. Sammes, et al, *J. Chem. Soc.* (C)., 1971, 2151–2155.

VIII-H Prepared from N-[[3-[4-[3-fluoro-4-(1-piperazinyl)]phenyl]-2-oxo-5-oxazolidinyl]methyl]-acetamide and piperonyl chloride using the general procedure from WO 93/23384, published Nov. 25, 1993, page 23, lines 19–28. Piperonyl chloride is commercially available.

VIII-I Prepared from N-[[3-[4-[3-fluoro4-(1-piperazinyl)]phenyl]-2-oxo-5-oxazolidinyl]methyl]-acetamide and the appropriate carboxylic acid using the general procedure of WO 95/14684, published Jun. 1, 1995, page 10, lines 4–17. The acids are commercially available.

VIII-J Prepared from N-[[3-[4-[3-fluoro-4-(1-piperazinyl)]phenyl]-2-oxo-5-oxazolidinyl]methyl]-acetamide and the appropriate isocyanate. The required isocyanates are commercially available.

CHART IX

IX-A Wherein $R^2$ is H; Prepared according to the procedures of PCT/US96/05202, filed Apr. 18, 1996, Examples 1, 2 and 3, page 12, line 11 through page 15, line 7.

IX-A Wherein $R^2$ is methyl; Prepared according to the general procedures of PCT/US96/05202, filed Apr. 18, 1996, Example 2, page 14, lines 16–32, but substituting methoxyacetyl chloride for benzyloxyacetyl chloride.

IX-A Wherein $R^2$ is benzyl; Prepared accroding to the procedures of PCT/US96/05202, filed Apr. 18, 1996. Example 2, page 14, lines 16–32.

IX-A Wherein $R^2$ is acetyl; Prepared according to the general procedures of PCT/US96/05202, filed Apr. 18, 1996, Example 2, page 14, lines 16–32, but substituting acetoxyacetyl chloride for benzyloxyacetyl chloride.

IX-B Using the general procedure of PCT/US96/05202, filed Apr. 18, 1996, Example 2, page 14, lines 16–32, but substituting the appropriate chloroformate for benzyloxyacetyl chloride.

IX-C Wherein $R^4$ is H; Prepared from (S)-N-[[3-[4-[cis-3,7-diazabicyclo[3.3.0]-octan-7-yl]-3-fluorophenyl]-2-oxo-5-oxazolidinyl]methyl]acetamide (PCT/US96/05202, filed Apr. 18, 1996, page 14, lines 21–24) using the general procedures from WO 93/23384, published Nov. 25, 1993, page 23, lines 4–16.

IX-C Wherein $R^4$ is all others listed; Using the general procedure of PCT/US96/05202, filed Apr. 18, 1996, Example 2, page 14, lines 16–32, but substituting the appropriate acid chloride in place of benzyloxyacetyl chloride.

IX-D Using the general procedure of PCT/US96/05202, filed Apr. 18, 1996, Example 2, page 14, lines 16–32, but substituting the appropriate sulfonyl chloride in place of benzyloxyacetyl chloride. The sulfonyl chlorides can be obtained as described for VIII-G.

IX-E Prepared from (S)-N-[[3-[4-[cis-3,7-diazabicyclo[3.3.0]octan-7-yl]-3-fluorophenyl]-2-oxo-5-oxazolidinyl]methyl]acetamide (PCT/US96/05202, filed Apr. 18, 1996, page 14, lines 21–24) and the appropriate carboxylic acid using the general procedures of WO 93/23384, published Nov. 25, 1993, page 18, lines 10–17. The appropriate carboxylic acids are commercially available.

IX-F Prepared by combining (S)-N-[[3-[4-[cis-3,7-diazabicyclo[3.3.0]octan-7-yl]-3-fluorophenyl]-2-oxo-5-oxazolidinyl]methyl]acetamide (PCT/US96/05202, filed Apr. 18, 1996, page 14, lines 21–24) and the appropriate isocyanate.

The required isocyanates are commercially available.

GENERAL PROCEDURE

The compounds of this invention are prepared by oxidation of a suitable precursor amine with any of a variety of oxidizing agents. Suitable oxidants include pertrifluoroacetic acid, meta-chloroperbenzoic acid (MCPBA), and magnesium monoperoxyphthalate (MMPP). For example, the synthesis is shown below for the case wherein $Q^1$ is morpholine and the oxidant is MMPP.

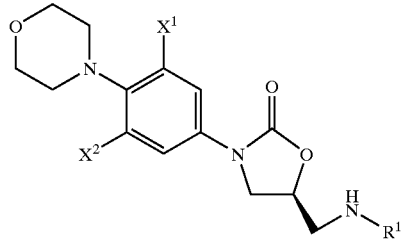
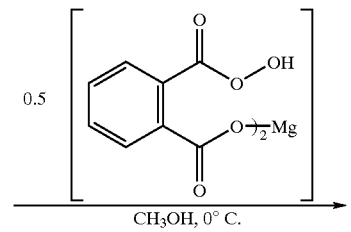

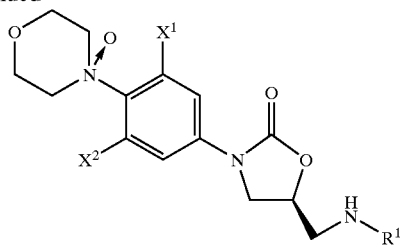

Oxidation of any of the oxazolidinones of Charts I–IX in which $Q^2$ is any of the other groups previously described is carried out similarly.

Charts X–XVIII show the final N-oxide compounds of the present invention which are prepared from the parent amines of Charts I–IX, respectively, by using the above General Procedures.

It will be apparent to those skilled in the art that the described synthetic procedures are merely representative in nature and that alternative synthetic processes are known to one of ordinary skill in organic chemistry.

The compounds of the present invention have an advantage over the parent amines in being exceedingly water soluble (see Table 1 below). For example, the compound of Example No. 2 has a solubility of 409 mg/ml. The parent amine has a water solubility of only 3.7 mg/ml. The N-oxide compounds of the present invention also retain all the in vitro and in vivo activities of the parent amines. The enhanced water solubility makes the N-oxide compounds of the present invention ideal for intravenous or injectable formulations

TABLE 1

Solubility Data for the N-oxides and parent amines.

| Example Number | Parent Amine Solubility (mg/mL) | N-Oxide Solubility (mg/mL) |
|---|---|---|
| 1 | 4.2 | 348 |
| 2 | 3.7 | 534 |
| 3 | 0.28 | 12.9 |
| 6 | 0.031 | 1.1 |

Procedure for Measuring Solubility:

In all solubility studies, an excess of compound is added to 0.5 to 1 ml of pH 7, 50 mM phosphate buffer or other vehicle of interest. The samples are capped and stirred via magnetic stir bars for 24 to 48 hours at room temperature. Samples are filter centrifuged (800×g) for 5–10 minutes through Millipore Ultrafree-MC 0.22 micron filter units. The supernate is analyzed by either UV or HPLC to quantitate the drug concentration. Results of the solubility testing of the compounds of the present invention are given above in Table 1.

The oxazolidinone compounds of the present invention have useful activity against a variety of microorganisms. The in vitro activity of compounds of the present invention are assessed by standard testing procedures such as the determination of minimum inhibitory concentration (MIC) by agar dilution as described in "Methods for Dilution Antimicrobial Susceptiblity Tests for Bacteria That Grow Aerobically" (MFT) published January 1993 by the National Committee for Clinical Laboratory Standards (NCCLS), 771 East Lancaster Avenue, Villanova, Pa. 19084, USA. The activity of selected compounds of the present invention against *Staphylococcus aureus* and *Streptococcus pneumoniae* are shown in Table 2.

TABLE 2

Activity of the N-oxides against *S. Aureus* and *S. Pneumoniae*.

| Example Number | MIC ($\mu$g/mL) S. Aureus UC® 9213 | MIC ($\mu$g/mL) S. Pneumoniae UC® 9912 |
|---|---|---|
| 1 | 2 | 0.5 |
| 2 | 4 | 1 |
| 3 | 4 | 1 |
| 4 | 2 | 0.5 |
| 5 | 4 | 0.5 |
| 6 | 2 | 0.25 |

As such, the compounds of the present invention are useful for treating microbial infections in humans or other warm-blooded animals by administering to a patient in need thereof an effective amount of a compound of Formula I. The compound is administered in a pharmaceutical composition orally, parenterally (such as subcutaneously or intravenously), or topically. Preferably the compound is administered in an amount of from about 0.1 to about 100 mg/kg of body weight/day, more preferably, from about 3.0 to about 50 mg/kg of body weight/day.

The following compounds of the present invention (with cross-references to the formulas in the charts below) are preferred:

| X-A | $R^1$=COCH$_3$, $X^1$=F, $X^2$=H: (S)-N-[[3-[3-fluoro-4-(1,1-dioxothiazolidin-3-yl)phenyl]-2-oxo-5-oxazolidinyl]methyl]acetamide N-oxide. |
|---|---|
| X-B | $R^1$=COCH$_3$, $X^1$=F, $X^2$=H: (S)-N-[[3-[3-fluoro-4-(3-oxazolidinyl)]phenyl]-2-oxo-5-oxazolidinyl]methyl]acetamide N-oxide. |
| XI-A | $R^1$=COCH$_3$, $X^1$=F, $X^2$=H: (S)-N-[[3-[3-fluoro-4-(1,1-dioxothiomorpholin-4-yl)phenyl]-2-oxo-5-oxazolidinyl]methyl]acetamide N-oxide |

-continued

| | |
|---|---|
| XI-C | $R^1$=COCH$_3$, $X^1$=F, $X^2$=H: (S)-N-[[3-[3-fluoro-4-[(1S,4S)-2-thia-2,2-dioxo-5-azabicyclo[2.2.1]heptan-5-yl]phenyl]-2-oxo-5-oxazolidinyl]methyl]acetamide N-oxide. |
| XII-A | $R^1$=COCH$_3$, $X^1$=F, $X^2$=F: (S)-N-[[3-[3,5-difluoro-4-morpholinyl]phenyl]-2-oxo-5-oxazolidinyl]methyl]acetamide N-oxide. |
| XII-A | $R^1$=COCH$_3$, $X^1$=F, $X^2$=H: (S)-N-[[3-[3-fluoro-4-morpholinyl]phenyl]-2-oxo-5-oxazolidinyl]methyl]acetamide N-oxide. |
| XII-A | $R^1$=COCH$_2$OH, $X^1$=F, $X^2$=H: (S)-N-[[3-[3-fluoro-4-morpholinyl]phenyl]-2-oxo-5-oxazolidinyl]methyl]hydroxyacetamide N-oxide. |
| XII-A | $R^1$=CHO, $X^1$=F, $X^2$=H: (S)-N-[[3-[3-fluoro-4-morpholinyl]phenyl]-2-oxo-5-oxazolidinyl]methyl]formamide N-oxide. |
| XII-A | $R^1$=CO$_2$CH$_3$, $X^1$=F, $X^2$=H: (S)-N-[[3-[3-fluoro-4-morpholinyl]phenyl]-2-oxo-5-oxazolidinyl]methyl]methylcarbamate N-oxide. |
| XII-A | $R^1$=COCH$_2$Cl$_2$, $X^1$=F, $X^2$=H: (S)-N-[[3-[3-fluoro-4-morpholinyl]phenyl]-2-oxo-5-oxazolidinyl]methyl]dichloroacetamide N-oxide. |
| XII-B | $R^1$=COCH$_3$, $X^1$=F, $X^2$=H: (S)-N-[[3-[3-fluoro-4-[(1S,4S)-2-oxa-5-azabicyclo[2.2.1]heptan-5-yl]phenyl]-2-oxo-5-oxazolidinyl]methyl]acetamide N-oxide. |
| XIII-C | $R^1$=COCH$_3$, $X^1$=F, $X^2$=H: (S)-N-[[3-[3-fluoro-4-(3-oxo-1-azetidinyl)phenyl]-2-oxo-5-oxazolidinyl]methyl]acetamide N-oxide. |
| XIII-H | $R^1$=COCH$_3$, $X^1$=F, $X^2$=H: (S)-N-[[3-[3-fluoro-4-(3-methoxy-3-methyl-1-azetidinyl)phenyl]-2-oxo-5-oxazolidinyl]methyl]acetamide N-oxide. |
| XIII-K | $R^1$=COCH$_3$, $X^1$=F, $X^2$=H, $R^3$=CH$_3$: (S)-N-[[3-[3-fluoro-4-[3-[(methoxycarbonyl)amino]-1-azetidinyl]phenyl]-2-oxo-5-oxazolidinyl]methyl]acetamide N-oxide. |
| XIII-J | $R^1$=COCH$_3$, $X^1$=F, $X^2$=H, $R^2$=H: (S)-N-[[3-[3-fluoro-4-[3-[(hydroxyacetyl)amino]-1-azetidinyl]phenyl]-2-oxo-5-oxazolidinyl]methyl]acetamide N-oxide. |
| XIV-E | $R^1$=COCH$_3$, $X^1$=F, $X^2$=H: (S)-N-[[3-[3-Fluoro-4-(3-hydroxypyrrolidinyl)phenyl]-2-oxo-5-oxazolidinyl]methyl]acetamide N-oxide. |
| XIV-J | $R^1$=COCH$_3$, $X^1$=F, $X^2$=H, $R^2$=H, $R^5$=CH$_3$: (S)-N-[[3-[3-Fluoro-4-(cis-3-(hydroxyacetylamino)-4-methylpyrrolidinyl)phenyl]-2-oxo-5-oxazolidinyl]methyl]acetamide N-oxide. |
| XIV-K | $R^1$=COCH$_3$, $X^1$=F, $X^2$=H, $R^3$=CH$_3$, $R^5$=CH$_3$: (S)-N-[[3-[3-Fluoro-4-(trans-3-(methoxycarbonylamino)-4-methylpyrrolidinyl)phenyl]-2-oxo-5-oxazolidinyl]methyl]acetamide N-oxide. |
| XV-B | $R^1$=COCH$_3$, $X^1$=F, $X^2$=H: (S)-N-[3-[4-(1,4-dioxa-8-aza-spiro[4.5]dec-8-yl)-3-fluoro-phenyl]-2-oxo-oxazolidin-5-ylmethyl]-acetamide N-oxide. |
| XV-D | $R^1$=COCH$_3$, $X^1$=F, $X^2$=H: (S)-N-[3-[3-fluoro-4-(2-hydroxymethyl-1,4-dioxa-8-aza-spiro-[4.5]dec-8-yl)-phenyl]-2-oxo-oxazolidin-5-ylmethyl]-acetamide N-oxide. |
| XV-M | $R^1$=COCH$_3$, $X^1$=F, $X^2$=H: (S)-1-[4-[5-(acetylaminomethyl)-2-oxo-oxazolidin-3-yl]-2-fluoro-phenyl-piperidine-4-carboxylic acid ethyl ester N-oxide. |
| XV-N | $R^1$=COCH$_3$, $X^1$=F, $X^2$=H: (S)-N-[3-[3-fluoro-4-(4-hydroxymethyl-piperidin-1-yl)-phenyl]-2-oxo-oxazolidin-5-ylmethyl]-acetamide N-oxide. |
| XVI-C | $R^1$=COCH$_3$, $X^1$=F, $X^2$=H: (S)-N-[3-[3-fluoro-4-(4-oxoazepin-1-yl)-phenyl]-2-oxo-oxazolidin-5-ylmethyl]-acetamide N-oxide. |
| XVII-B | $R^1$=COCH$_3$, $X^1$=H, $X^2$=H, $R^3$=CH$_3$: (S)-4-(4-(5-((acetylamino)methyl)-2-oxo-3-oxazolidinyl)phenyl)-1-piperazinecarboxylic acid, methyl ester N-oxide. |
| XVII-B | $R^1$=COCH$_3$, $X^1$=F, $X^2$=H, $R^3$=CH$_2$CH$_3$: (S)4-(4-(5-((acetylamino)methyl)-2-oxo-3-oxazolidinyl)-2-fluorophenyl)-1-piperazinecarboxylic acid, ethyl ester N-oxide. |
| XVIII-A | $R^1$=COCH$_3$, $X^1$=F, $X^2$=H, $R^2$=H: (S)-N-[[3-[3-fluoro-4-[cis-3-(hydroxyacetyl)-3,7-diazabicyclo[3.3.0]octan-7-yl]phenyl]-2-oxo-5-oxazolidinyl]methyl]acetamide N-oxide. |
| XVIII-C | $R^1$=COCH$_3$, $X^1$=F, $X^2$=H, $R^4$=cyclopropyl: (S)-N-[[3-[3-fluoro-4-[cis-3-[(cyclopropyl)carbonyl]-3,7-diazabicyclo[3.3.0]octan-7-yl]phenyl]-2-oxo-5-oxazolidinyl]methyl]acetamide N-oxide. |
| XVIII-D | $R^1$=COCH$_3$, $X^1$=F, $X^2$=H, $R^9$=CH$_3$: (S)-N-[[3-[3-fluoro-4-[cis-3-(methylsulfonyl)-3,7-diazabicyclo[3.3.0]octan-7-yl]phenyl]-2-oxo-5-oxazolidinyl]methyl]acetamide N-oxide. |
| XVII-A | $R^1$=COCH$_3$, $R^2$=H, $X^1$=$X^2$=F: (S)-N-[[3-[3,5-difluoro-4-[4-(hydroxyacetyl)-1-piperazinyl]phenyl]-2-oxo-5-oxazolidinyl]-methyl]acetamide N-oxide. |
| XVII-A | $R^1$=COCH$_3$, $R^2$=H, $X^1$=F, $X^2$=H: (S)-N-[[3-[3-fluoro-4-[4-(hydroxyacetyl)-1-piperazinyl]phenyl]-2-oxo-5-oxazolidinyl]-methyl]acetamide N-oxide. |
| XVII-B | $R^1$=COCH$_3$, $R^3$=CH$_3$, $X^1$=$X^2$=F: (S)-4-[4-5-[(acetylamino)methyl]-2-oxo-3-oxazolidinyl]-2,6-difluorophenyl]-1-piperazinecarboxylic acid, methyl ester N-oxide. |

-continued

| | |
|---|---|
| XVII-B | $R^1$=COCH$_3$, $R^3$=CH$_3$, $X^1$=F, $X^2$=H: (S)-4-[4-[5-[(acetylamino)-methyl]-2-oxo-3-oxazolidinyl]-2-fluorophenyl]-1-piperazinecarboxylic acid, methyl ester N-oxide. |

The following compounds of the present invention (with cross references to the formulas in the charts below) are most preferred:

| | |
|---|---|
| XII-A | $R^1$=COCH$_3$, $X^1$=$X^2$=F: (S)-N-[[3-[3,5-difluoro-4-morpholinyl]phenyl]-2-oxo-5-oxazolidinyl]methyl]acetamide N-oxide; |
| XII-A | $R^1$=COCH$_3$, $X^1$=F, $X^2$=H: (S)-N-[[3-[3-fluoro-4-morpholinyl]phenyl]-2-oxo-5-oxazolidinyl]methyl]acetamide N-oxide; |
| XVII-A | $R^1$=COCH$_3$, $R^2$=H, $X^1$=$X^2$=F: (S)-N-[[3-[3,5-difluoro-4-[4-(hydroxyacetyl)-1-piperazinyl]phenyl]-2-oxo-5-oxazolidinyl]-methyl]acetamide N-oxide; |
| XVII-A | $R^1$=COCH$_3$, $R^2$=H, $X^1$=F, $X^2$=H: (S)-N-[[3-[3-fluoro-4-[4-(hydroxyacetyl)-1-piperazinyl]phenyl]-2-oxo-5-oxazolidinyl]-methyl]acetamide N-oxide; |
| XVII-B | $R^1$=COCH$_3$, $R^3$=CH$_3$, $X^1$=$X^2$=F: (S)-4-[4-[5-[(acetylamino)methyl]-2-oxo-3-oxazolidinyl]-2,6-difluorophenyl]-1-piperazinecarboxylic acid, methyl ester N-oxide; |
| XVII-B | $R^1$=COCH$_3$, $R^3$=CH$_3$, $X^1$=F, $X^2$=H: (S)-4-[4-[5-[(acetylamino)-methyl]-2-oxo-3-oxazolidinyl]-2-fluorophenyl]-1-piperazinecarboxylic acid, methyl ester N-oxide. |

DESCRIPTION OF PREFERRED EMBODIMENTS

EXAMPLE 1

(S)-N-[[3-[3-Fluoro-4-[4-(hydroxyacetyl)-1-piperazinyl]phenyl]-2-oxo-5-oxazolidinyl]-methyl]acetamide N-oxide

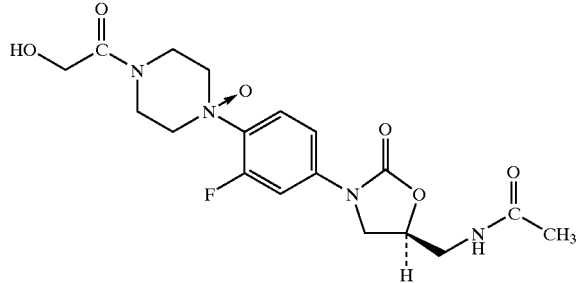

(S)-N-[[3-[3-Fluoro-4-[4-(hydroxyacetyl)-1-piperazinyl]-phenyl]-2-oxo-5-oxazolidinyl]methyl]-acetamide (VIII-A, $R^1$=COCH$_3$, $R^2$=H, $X^1$=F, $X^2$=H) (11.8 g) is dissolved in 200 mL of methanol. Monoperoxyphthalic acid, magnesium salt hexahydrate (80% pure, 18.5 g) is added and the resulting suspension is stirred at 25° C. for two hours. The reaction is filtered and the filtrate is concentrated to afford a white solid. This solid is chromatographed on silica gel using 20% methanol in chloroform as eluent to afford the N-oxide. Lyophilization of this material affords the purified product as a hydrate (9.5 g).

Physical characteristics are as follows:

Mp 158–160° C.; IR (mull) 3276, 3071, 1754, 1658, 1622, 1502, 1444, 1410, 1286, 1255, 1224, 1204, 1135, 1095, 752 cm$^{-1}$; MS (FAB) m/z 411, 565, 412, 411, 396, 395, 394, 393, 392, 335, 56.

EXAMPLE 2

S)-N-[[3-[3-Fluoro-4-(4-morpholinyl)phenyl]-2-oxo-5-zolidinyl]methyl]acetamide N-oxide

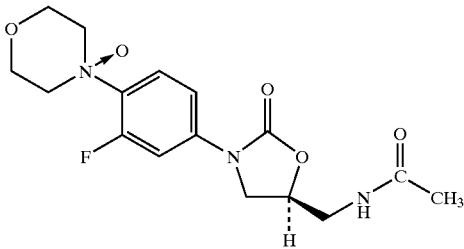

(S)-N-[[3-[3-Fluoro-4-(4-morpholinyl)phenyl]-2-oxo-5-oxazolidinyl]methyl]-acetarnide (III-A, $R^1$=COCH$_3$, $X^1$=F, $X^2$=H) (12.5 g) is suspended in 200 mL of methanol. Monoperoxyphthalic acid, magnesium salt hexahydrate (80% pure, 11.5 g) is added and the resulting suspension is stirred at 25° C. for two hours. The reaction mixture is filtered and the filtrate is concentrated to afford a light-yellow solid. This material is chromatographed on silica gel using 10% methanol (saturated with ammonia) in chloroform as eluent to afford 8.75 g of the N-oxide.

Physical characteristics are as follows:

Mp 202–204° C.; IR (mull) 1747, 1669, 1620, 1556, 1508, 1495, 1445, 1413, 1341, 1295, 1269, 1232, 1204, 1124, 755 cm$^{-1}$; MS (FAB) m/z 354, 708, 707, 355, 354, 339, 338, 337, 336, 86, 56. Anal. Found: C, 53.99; H, 5.70; N, 11.76.

EXAMPLE 3

(S)-N-[[3-[3-Fluoro4-[4-(methylsulfonyl)-1-piperazinyl]phenyl]-2-oxo-5-oxazolidinyl]-methyl]acetamide N-oxide

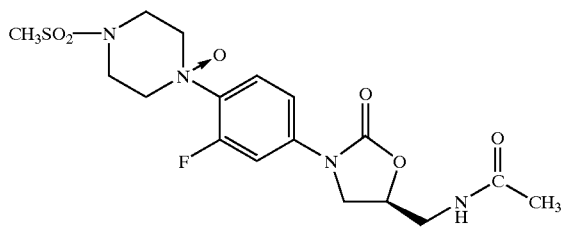

Pertrifluoroacetic acid is prepared in situ by the addition of 30% $H_2O_2$ solution (0.15 mL) to trifluoroacetic anhydride (0.45 mL) in 5 mL of methylene chloride at 0° C. This solution is stirred at 0° C. for ten minutes, at 25° C. for 30 minutes and then cooled back to 0° C. (S)-N-[[3-[3-fluoro-4-[4-(methylsulfonyl)-1-piperazinyl]phenyl]-2-oxo-5-oxazolidinyl]-methyl]acetamide (VIII-G, $R^1$=COCH$_3$, $R^9$=CH$_3$, $X^1$=F, $X^2$=H) (0.207 g) is added and the reaction is stirred at 25° C. for 30 minutes and then concentrated. The residue is chromatographed on silica gel using 10% methanol (saturated with ammonia) in chloroform as the eluent to afford 0.14 g of the N-oxide as a hydrate.

Physical characteristics are as follows:

Mp 168–170° C.; IR (mull) 1751, 1668, 1658, 1503, 1443, 1408, 1340, 1328, 1277, 1260, 1226, 1157, 1130, 1081,855 cm$^{-1}$; MS (FAB) m/z 431, 862, 861, 432, 431, 416, 415, 414, 413, 335, 56.

EXAMPLE 4

(S)-N-[[3-[3,5-Difluoro-4-[4-(hydroxyacetyl)-1-piperazinyl]phenyl]-2-oxo-5-oxazolidinyl]-methyl]acetamide N-oxide

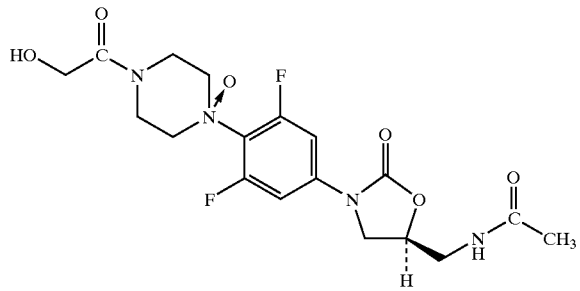

(S)-N-[[3-[3,5-Difluoro-4-[4-(hydroxyacetyl)-1-piperazinyl]-phenyl]-2-oxo-5-oxazolidinyl]methyl]-acetamide (VIII-A, $R^1$=COCH$_3$, $R^2$=H, $X^1$=$X^2$=F) (0.13 g) is dissolved in 5 mL of methanol. Monoperoxyphthalic acid, magnesium salt hexahydrate (80% pure, 0.2 g) is added and the resulting suspension is stirred at 25° C. for 72 hours. An additional 0.2 g of monoperoxyphthalic acid is added and the reaction is stirred an additional 48 hours. The reaction mixture is filtered and the filtrate is concentrated to afford a light-yellow oil. This material is chromatographed on silica gel using 20% methanol (saturated with ammonia) in chloroform as eluent to afford 55 mg of the N-oxide.

Physical characteristics are as follows:

Mp 100–105° C.; IR (mull) 3292, 1757, 1658, 1636, 1584, 1557, 1497, 1413, 1287, 1245, 1213, 1098, 1054, 1043, 1020 cm$^{-1}$; MS (FAB) m/z 429 (M+H), 857, 429, 413, 412, 411, 353, 161, 145, 73, 56.

EXAMPLE 5

(S)-N-[[3-[4-[4-[(Cyanomethyl)sulfonyl]-1-piperazinyl]-3-fluorophenyl]-2-oxo-5-oxazolidinyl]methyl]acetamide N-oxide

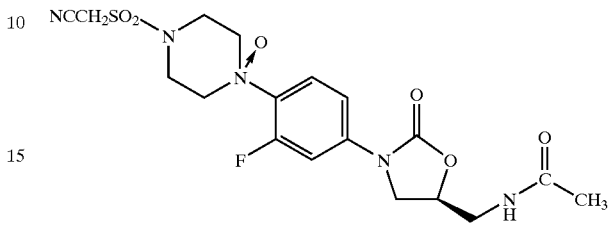

(S)-N-[[3-[4-[4-[(cyanomethyl)sulfonyl]-1-piperazinyl]-3-fluorophenyl]-2-oxo-5-oxazolidinyl]methyl]acetamide (VIII-G, $R^1$=COCH$_3$, $R^9$=NCCH$_2$, $X^1$=F, $X^2$=H) (0.550 g) is dissolved in 15 mL of methanol. Monoperoxyphthalic acid, magnesium salt hexahydrate (80% pure, 0.616 g) is added and the reaction is stirred at room temperature for 4 hours. The reaction is then filtered and the filtrate is concentrated to afford an oil. This oil is chromatographed on silica gel using 10% methanol (saturated with ammonia) in chloroform as eluent to afford 0.42 g of the N-oxide.

Physical characteristics are as follows:

Mp 153–156° C. IR (mull) 1748, 1656, 1625, 1503, 1443, 1406, 1357, 1342, 1257, 1224, 1161, 1148, 1137, 931, 756 cm$^{-1}$; MS (FAB) m/z 456 (M+H), 457, 456, 441, 440, 439, 438, 336, 335, 91, 56.

EXAMPLE 6

(S)-N-[[3-[4-[4-[(2-Cyanophenyl)sulfonyl]-1-piperazinyl]-3-fluorophenyl]-2-oxo-5-oxazolidinyl]methyl]acetamide N-oxide

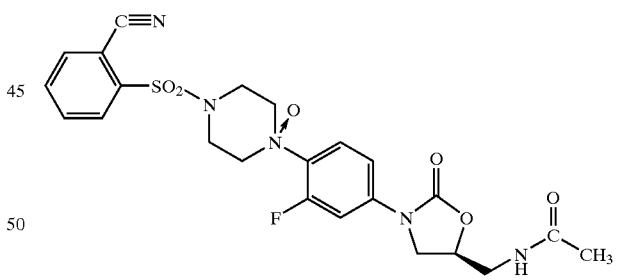

(S)-N-[[3-[4-[4-[(2-cyanophenyl)sulfonyl]-1-piperazinyl]-3-fluorophenyl]-2-oxo-5-oxazolidinyl]methyl]acetamide (VIII-G, $R^1$=COCH$_3$, $R^9$=2-cyanophenyl, $X^1$=F, $X^2$=H) (0.5 g) is suspended in 10 mL of methanol. Monoperoxyphthalic acid, magnesium salt hexahydrate (80% pure, 0.616 g) is added and the reaction mixture is stirred at room temperature for 2 hours. The reaction is concentrated and the resulting oil is chromatographed on silica gel using 7% methanol (saturated with ammonia) in chloroform as eluent to afford 0.33 g of the N-oxide.

Physical characteristics are as follows:

Mp 190–192° C. IR (mull) 1756, 1678, 1661, 1620, 1500, 1486, 1408, 1280, 1256, 1222, 1181, 1168, 1129, 1082, 924 cm$^{-1}$; MS (FAB) m/z 518 (M+H), 520, 519, 518, 503, 502, 501, 500, 336, 335, 56.

EXAMPLE 7

Reduction of the N-oxide of Example 2 in vivo Following Intravenous and Oral Administration to Rats The rate and extent of reduction of the N-oxide of Example 2 was investigated in vivo using the following procedures: Six male Sprague-Dawley rats are used for this study. Three rats are given a single intravenous 10 mg/kg dose of the N-oxide and three rats are given a single oral 25 mg/kg dose of the N-oxide. Blood is collected pre-dose and up to 24 h post dose. The plasma is analyzed for the N-oxide and the parent amine by LC-MS.

Results:

Only traces of the N-oxide were found in plasma in the first time point immediately post intravenous injection. The parent amine was detected in plasma up to 10 h post dosing. The lower limit of quantitation for the assay was ≈0.01 μg/mL. Because the N-oxide was reduced to the parent amine so rapidly, pharmacokinetic parameters were measured for the parent amine rather than for the N-oxide.

After both intravenous and oral dosing of the N-oxide, the Cmax, Tmax and AUC values for the parent amine were very similar to those found when the parent amine compound was administered directly to rats using the same doses and protocol. The relative bioavailability of the parent amine from the orally administered N-oxide was approximately 100% when compared to orally administered parent amine. The rapid and essentially quantitative conversion of the N-oxide to the parent amine in vivo demonstrates that the N-oxide is a suitable pro-drug for the parent amine.

FORMULA CHART

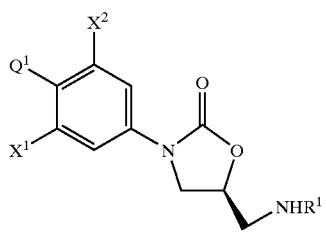

I

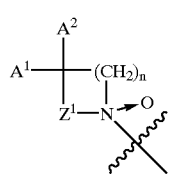

II

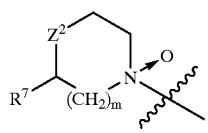

III

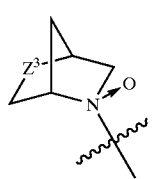

IV

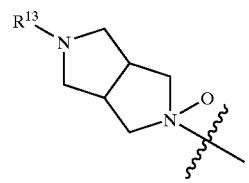

V

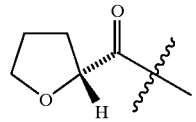

VI

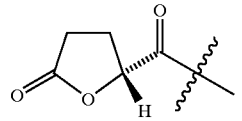

VII

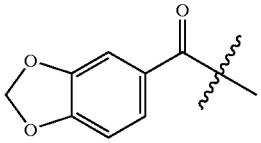

VIII

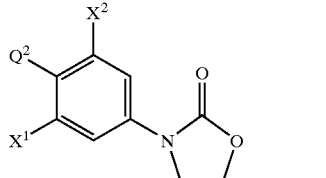

IX

CHART I - THIAZOLIDINES

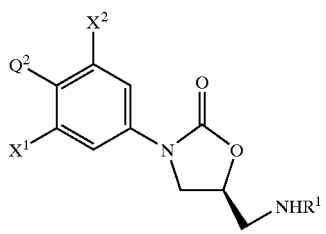

IX wherein Q$^2$ is

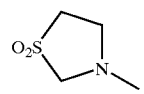

I-A

I-B wherein X$^1$ and X$^2$ are independently
—H,
—F, or
—Cl;
wherein R$^1$ is
—CHO,
—COCH$_3$,
—COCHCl$_2$, —COCHF$_2$,
—CO$_2$CH$_3$,
—SO$_2$CH$_3$, or
—COCH$_2$OH.

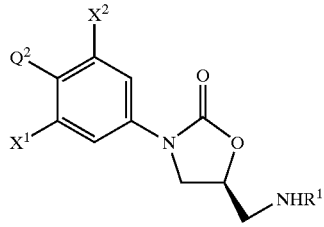

wherein Q$^2$ is

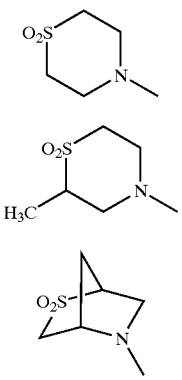

II-A

II-B

II-C wherein X$^1$ and X$^2$ are independently

—H,
—F, or
—Cl;

wherein R$^1$ is

—CHO,
—COCH$_3$,
—COCHCl$_2$,
—COCHF$_2$,
—CO$_2$CH$_3$,
—SO$_2$CH$_3$, or
—COCH$_2$OH.

CHART III - MORPHOLINES -BRIDGES MORPHOLINES

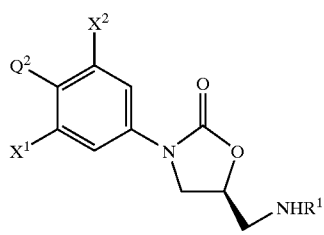

IX wherein Q$^2$ is

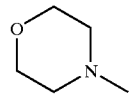

III-A

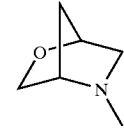

III-B wherein X$^1$ and X$^2$ are independently

—H,
—F, or
—Cl;

wherein R$^1$ is

—CHO,
—COCH$_3$,
—COCHCl$_2$,
—COCHF$_2$,
—CO$_2$CH$_3$,
—SO$_2$CH$_3$, or
—COCH$_2$OH.

CHART IV - AZETIDINES

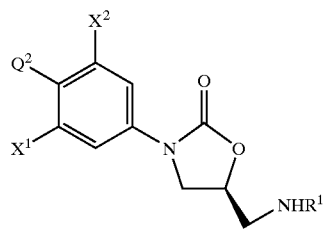

IX wherein Q$^2$ is

IV-A

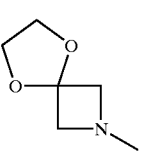

IV-B

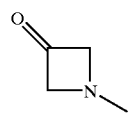

IV-C

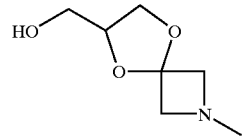

IV-D

-continued

IV-E 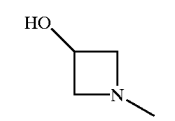

IV-F 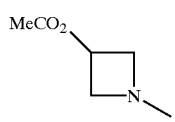

IV-G 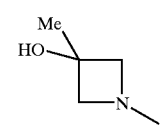

IV-H 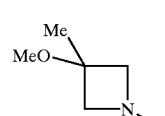

IV-I

IV-J 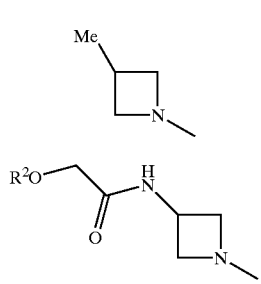

IV-K

IV-L 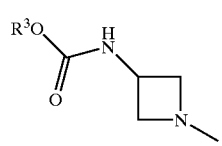

IV-M 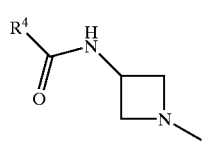

IV-N 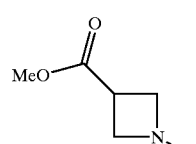

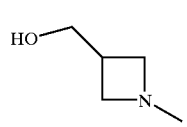

wherein $X^1$ and $X^2$ are independently
—H,
—F, or
—Cl;
wherein $R^1$ is —CHO,
—COCH$_3$,
—COCHCl$_2$,
—COCHF$_2$,
—CO$_2$CH$_3$,
—SO$_2$CH$_3$, or
—COCH$_2$OH;
wherein $R^2$ is
—H,
—CH$_3$,
—CH$_2$Ph, or
—COCH$_3$;
wherein $R^3$ is —CH$_3$,
—CH$_2$CH$_3$,
—CH$_2$CH$_2$CH$_3$, or
-phenyl;
wherein $R^4$ is
—H,
—CH$_3$,
—CH$_2$CH$_3$,
—CH$_2$CH$_2$CH$_3$,
—CH$_2$CH$_2$CH$_2$CH$_3$,
-phenyl,
—CH$_2$Cl,
—CHCl$_2$,
CH$_2$F,
—CHF$_2$,
-substituted aryl,
—CH$_2$—(aryl), or
-cycloalkyl (rings of 3–6 carbons).

CHART V - PYRROLIDINES

IX 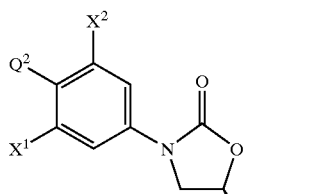

wherein $Q^2$ is

V-A 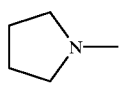

V-B 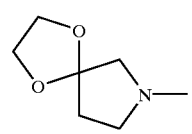

V-C 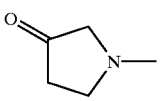

V-D 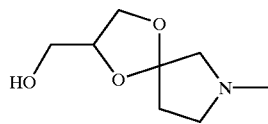

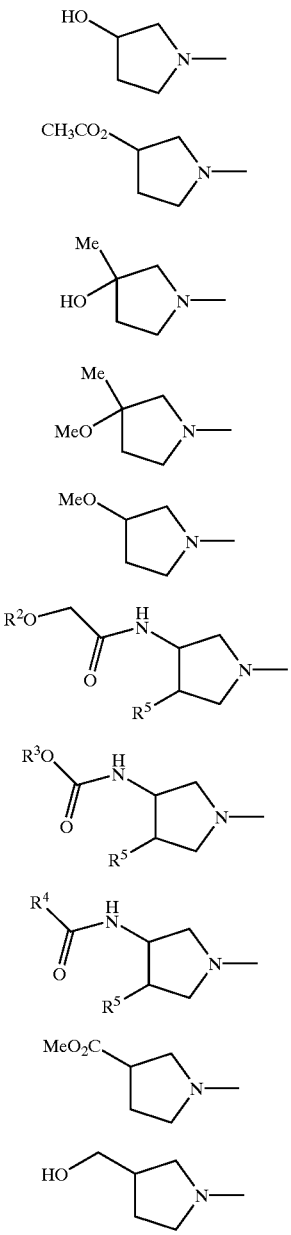

wherein X¹ and X² are independently
—H,
—F, or
—Cl;
wherein R¹ is
—CHO,
—COCH₃,
—COCHCl₂,
—COCHF₂,
—CO₂CH₃,
—SO₂CH₃, or
—COCH₂OH;
wherein R² is
—H,
—CH₃,
—CH₂Ph, or
—COCH₃;
wherein R³ is
—CH₃,
—CH₂CH₃,
—CH₂CH₂CH₃, or
-phenyl;
wherein R⁴ is
—H,
—CH₃,
—CH₂CH₃,
—CH₂CH₂CH₃,
—CH₂CH₂CH₂CH₃,
-phenyl,
—CH₂Cl,
—CHCl₂,
CH₂F,
—CHF₂,
-substituted aryl,
—CH₂—(aryl), or
-cycloalkyl (rings of 3–6 carbons);
wherein R⁵ is
—H,
—CH₃,
—CH₂CH₃, or
—CH₂CH₂CH₃.

CHART VI - PIPERIDINES

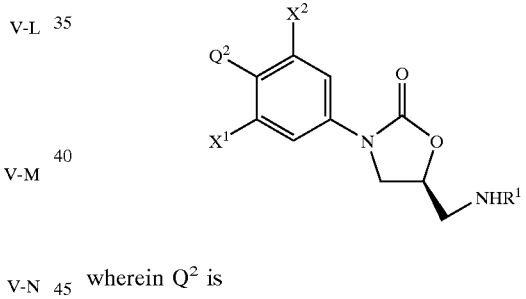

IX

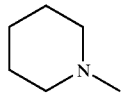

VI-A

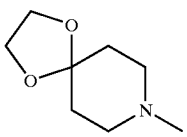

VI-B

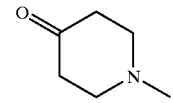

VI-C

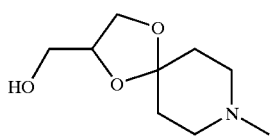

VI-D

-continued

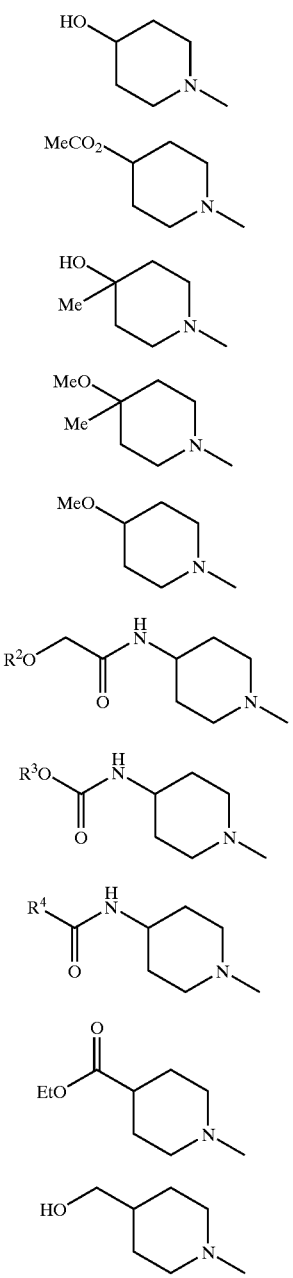

wherein X¹ and X² are independently
—H,
—F, or
—Cl;

wherein R¹ is
—CHO,
—COCH₃,
—COCHCl₂,
—COCHF₂,
—CO₂CH₃,
—SO₂CH₃, or
COCH²OH;

wherein R² is
—H,
—CH₃,
—CH₂Ph, or
—COCH₃;

wherein R³ is
—CH₃,
—CH₂CH₃,
—CH₂CH₂CH₃, or
-phenyl;

wherein R⁴ is
—H,
—CH₃,
—CH₂CH₃,
—CH₂CH₂CH₃,
—CH₂CH₂CH₂CH₃,
-phenyl,
—CH₂Cl,
—CHCl₂,
CH₂F,
—CHF₂,
-substituted aryl,
—CH₂—(aryl), or
-cycloalkyl (rings of 3–6 carbons).

CHART VII - AZEPINES

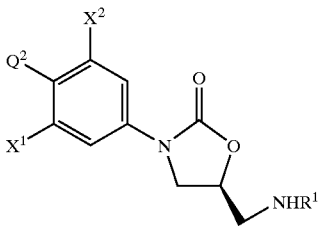

IX wherein Q² is

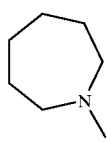

VII-A

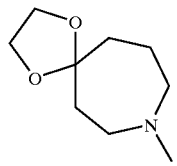

VII-B

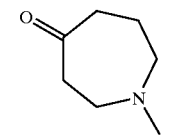

VII-C

-continued

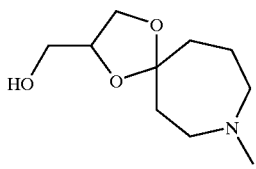

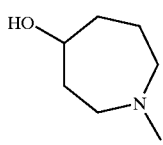

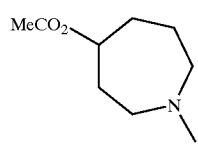

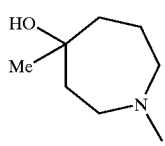

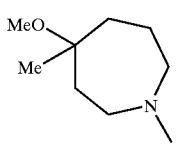

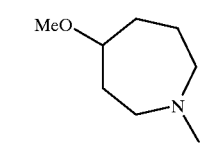

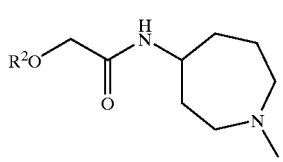

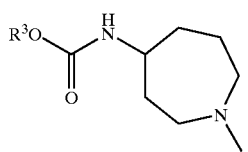

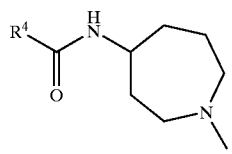

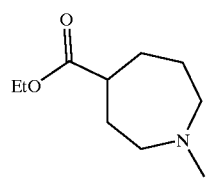

VII-D

VII-E

VII-F

VII-G

VII-H

VIII-I

VII-J

VII-K

VII-L

VII-M

-continued

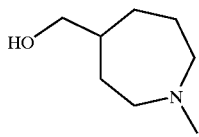

VII-N wherein $X^1$ and $X^2$ are independently
—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, or
—COCH$_2$OH;
wherein $R^2$ is
—H,
—CH$_3$,
—CH$_2$Ph, or
—COCH$_3$;
wherein $R^3$ is
—CH$_3$,
—CH$_2$CH$_3$,
—CH$_2$CH$_2$CH$_3$, or
-phenyl;
wherein $R^4$ is
—H,
—CH$_3$,
—CH$_2$CH$_3$,
—CH$_2$CH$_2$CH$_3$,
—CH$_2$CH$_2$CH$_2$CH$_3$,
-phenyl,
—CH$_2$Cl,
—CHCl$_2$,
CH$_2$F,
—CHF$_2$,
-substituted aryl,
—CH$_2$—(aryl), or
-cycloalkyl (rings of 3–6 carbons).

CHART VIII - PIPERAZINES

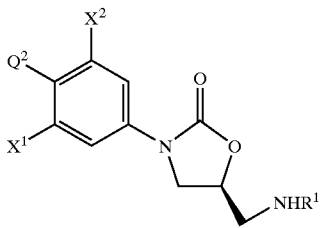

IX wherein $Q^2$ is

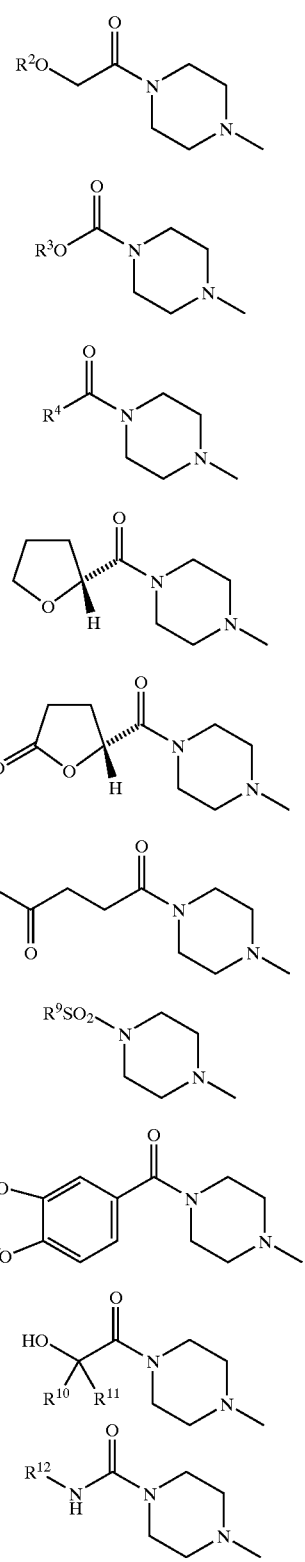

VIII-A
VIII-B
VIII-C
VIII-D
VIII-E
VIII-F
VIII-G
VIII-H
VIII-I
VIII-J wherein $X^1$ and $X^2$ are independently
- —H,
- —F, or
- —Cl;

wherein $R^1$ is
- —CHO,
- —COCH$_3$,
- —COCHCl$_2$,
- —COCHF$_2$,
- —CO$_2$CH$_3$,
- —SO$_2$CH$_3$, or
- —COCH$_2$OH;

wherein $R^2$ is
- —H,
- —CH$_3$,
- —CH$_2$Ph, or
- —COCH$_3$;

wherein $R^3$ is
- —CH$_3$,
- —CH$_2$CH$_3$,
- —CH$_2$CH$_2$CH$_3$, or
- -phenyl;

wherein $R^4$ is
- —H,
- —CH$_3$,
- —CH$_2$CH$_3$,
- —CH$_2$CH$_2$CH$_3$,
- —CH$_2$CH$_2$CH$_2$CH$_3$,
- -phenyl,
- —CH$_2$Cl,
- —CHCl$_2$,
- CH$_2$F,
- —CHF$_2$,
- -substituted aryl,
- —CH$_2$—(aryl), or
- -cycloalkyl (rings of 3–6 carbons);

wherein $R^9$ is
- —CH$_3$,
- —CH$_2$Cl,
- —CH$_2$CH=CH$_2$,
- substituted aryl, or
- —CH$_2$CN;

wherein $R^{10}$ and $R^{11}$ are independently
- —H,
- —CH$_3$, or
- -together form a cyclopropyl ring;

wherein $R^{12}$ is
- —CH$_2$Ph, or
- -substituted aryl.

CHART IX - PYRROLOPYRROLIDINES

IX

[Structure: phenyl ring with X¹, X², Q² substituents connected to oxazolidinone-CH₂-NHR¹]

wherein Q² is

IX-A [Structure: R²O-C(O)-CH₂-N(pyrrolopyrrolidine)-N-CH₃]

IX-B [Structure: R³O-C(O)-N(pyrrolopyrrolidine)-N-CH₃]

IX-C [Structure: R⁴-C(O)-N(pyrrolopyrrolidine)-N-CH₃]

IX-D [Structure: R⁹SO₂-N(pyrrolopyrrolidine)-N-CH₃]

IX-E [Structure: HO-C(R¹⁰)(R¹¹)-C(O)-N(pyrrolopyrrolidine)-N-CH₃]

IX-F [Structure: R¹²-NH-C(O)-N(pyrrolopyrrolidine)-N-CH₃]

wherein X¹ and X² are independently
- —H,
- —F, or
- —Cl;

wherein R¹ is
- —CHO,
- —COCH₃,
- —COCHCl₂,
- —COCHF₂,
- —CO₂CH₃,
- —SO₂CH₃, or
- —COCH²OH;

wherein R² is
- —H,
- —CH₃,
- —CH₂Ph, or
- —COCH₃;

wherein R³ is
- —CH₃,
- —CH₂CH₃,
- —CH₂CH₂CH₃, or
- -phenyl;

wherein R⁴ is
- —H,
- —CH₃,
- —CH₂CH₃,
- —CH₂CH₂CH₃,
- —CH₂CH₂CH₂CH₃,
- -phenyl,
- —CH₂Cl,
- —CHCl₂,
- —CH₂F,
- —CHF₂,
- -substituted aryl,
- —CH₂—(aryl), or
- -cycloalkyl (rings of 3–6 carbons);

wherein R⁹ is
- —CH₃,
- —CH₂Cl,
- —CH₂CH=CH₂,
- substituted aryl, or
- —CH₂CN;

wherein R¹⁰ and R¹¹ are independently
- —H,
- —CH₃, or
- -together form a cyclopropyl ring;

wherein R¹² is
- —CH₂Ph, or
- -substituted aryl.

CHART X - THIAZOLIDINES

I

[Structure: phenyl ring with X¹, X², Q² substituents connected to oxazolidinone-CH₂-NHR¹]

wherein $Q^1$ is

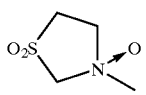

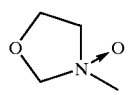

wherein $X^1$ and $X^2$ are independently
- —F, or
- —Cl;

wherein $R^1$ is
- —CHO,
- —COCH$_3$,
- —COCHCl$_2$,
- —COCHF$_2$,
- —CO$_2$CH$_3$,
- —SO$_2$CH$_3$, or
- —COCH$_2$OH.

CHART XI - THIOMORPHOLINES - BRIDGED THIOMORPHOLINES

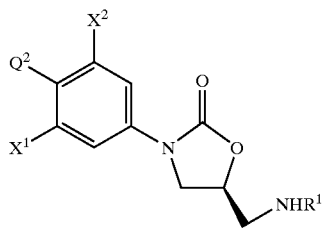 I wherein $Q^1$ is

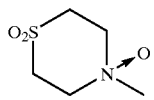 XI-A

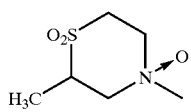 XI-B

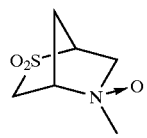 XI-C wherein $X^1$ and $X^2$ are independently
- —H,
- —F, or
- —Cl;

wherein $R^1$ is
- —CHO,
- —COCH$_3$,
- —COCHCl$_2$,
- —COCHF$_2$,
- —CO$_2$CH$_3$,
- —SO$_2$CH$_3$, or
- —COCH$_2$OH.

CHART XII - MORPHOLINES - BRIDGED MORPHOLINES

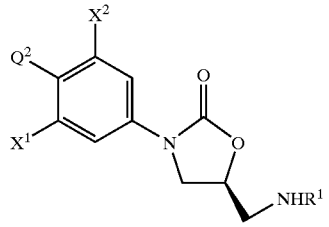 I wherein $Q^1$ is

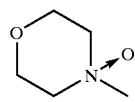 XII-A

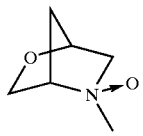 XII-B wherein $X^1$ and $X^2$ are independently
- —H,
- —F, or
- —Cl;

wherein $R^1$ is
- —CHO,
- —COCH$_3$,
- —COCHCl$_2$,
- —COCHF$_2$,
- —CO$_2$CH$_3$,
- —SO$_2$CH$_3$, or
- —COCH$_2$OH.

CHART XIII - AZETIDINES

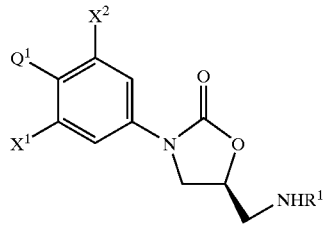 I wherein $Q^1$ is

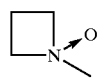 XIII-A

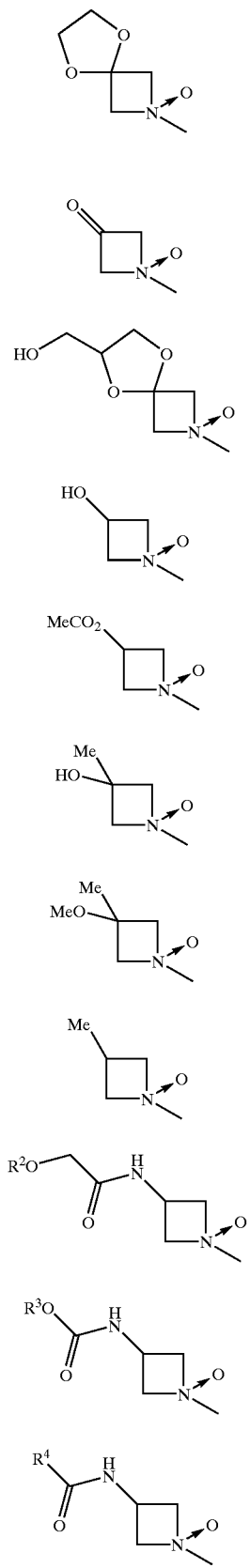

wherein $X^1$ and $X^2$ are independently

—H,
—F, or
—Cl;

wherein $R^1$ is

—CHO,
—COCH$_3$,
—COCHCl$_2$,
—COCHF$_2$,
—CO$_2$CH$_3$,
—SO$_2$CH$_3$, or
—COCH$_2$OH;

wherein $R^2$ is

—CH$_3$,
—CH$_2$Ph, or
—COCH$_3$;

wherein $R^3$ is

—CH$_3$,
—CH$_2$CH$_3$,
—CH$_2$CH$_2$CH$_3$, or
-phenyl;

wherein $R^4$ is

—H,
—CH$_3$,
—CH$_2$CH$_3$,
—CH$_2$CH$_2$CH$_3$,
—CH$_2$CH$_2$CH$_2$CH$_3$,
-phenyl,
—CH$_2$Cl,
—CHCl$_2$,
CH$_2$F,
—CHF$_2$,
-substituted aryl,
—CH$_2$-(aryl), or
-cycloalkyl (rings of 3–6 carbons).

CHART XIV - PYRROLIDINES

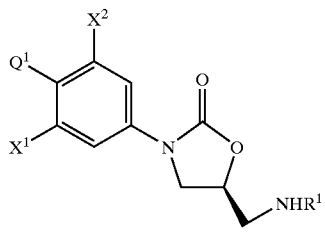

wherein $Q^1$ is

XIV-A
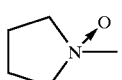

XIV-B

XIV-C
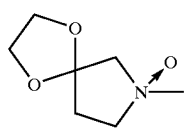

XIV-D

XIV-E

XIV-F 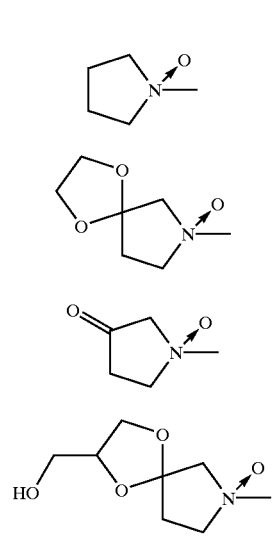

XIV-G

XIV-H

XIV-I

XIV-J 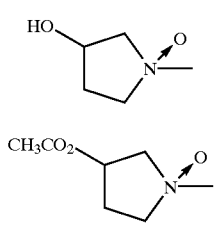

XIV-K 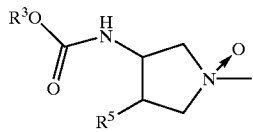

XIV-L 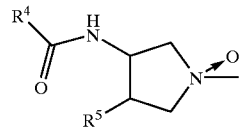

XIV-M 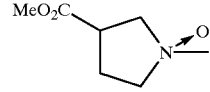

XIV-N wherein $X^1$ and $X^2$ are independently
—H,
—F, or
—Cl;
wherein $R^1$ is
—CHO,
—COCH$_3$,
—COCHCl$_2$,
—COCHF$_2$,
—CO$_2$CH$_3$,
—SO$_2$CH$_3$, or
—COCH$_2$OH;
wherein $R^2$ is
—H,
—CH$_3$,
—CH$_2$Ph, or
—COCH$_3$;
wherein $R^3$ is
—CH$_3$,
—CH$_2$CH$_3$,
—CH$_2$CH$_2$CH$_3$, or
-phenyl;
wherein $R^4$ is
—H,
—CH$_3$,
—CH$_2$CH$_3$,
—CH$_2$CH$_2$CH$_3$,
—CH$_2$CH$_2$CH$_2$CH$_3$,
-phenyl,
—CH$_2$Cl,
—CHCl$_2$,
CH$_2$F,
—CHF$_2$,
-substituted aryl,
—CH$_2$—(aryl), or
cycloalkyl (rings of 3–6 carbons);
wherein $R^5$ is
—H,
—CH$_3$, —CH₂CH₃, or
—CH₂CH₂CH₃.
CHART XV - PIPERIDINES
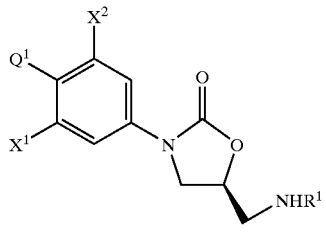
wherein Q¹ is
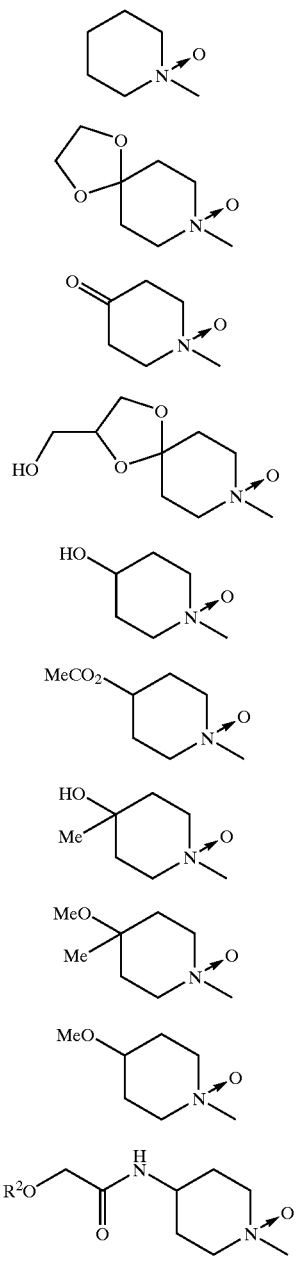
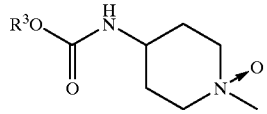
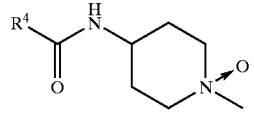
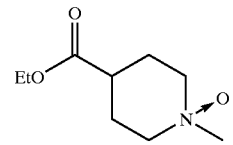
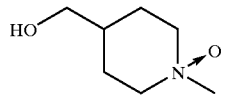
wherein X¹ and X² are independently
- —H,
- —F, or
- —Cl;
wherein R¹ is
- —CHO,
- —COCH₃,
- —COCHCl₂,
- —COCHF₂,
- —CO₂CH₃,
- —SO₂CH₃, or
- COCH₂OH;
wherein R² is
- —H,
- —CH₃,
- —CH₂Ph, or
- —COCH₃;
wherein R³ is
- —CH₃,
- —CH₂CH₃,
- —CH₂CH₂CH₃, or
- -phenyl;
wherein R⁴ is
- —H,
- —CH₃,
- —CH₂CH₃,
- —CH₂CH₂CH₃,
- —CH₂CH₂CH₂CH₃,
- -phenyl,
- —CH₂Cl,
- —CHCl₂,
- CH₂F,
- —CHF₂,
- -substituted aryl, —CH₂—(aryl), or
-cycloalkyl (rings of 3–6 carbons).
CHART XVI - AZEPINES
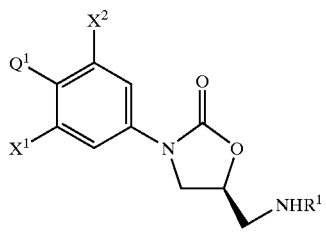
wherein Q¹ is
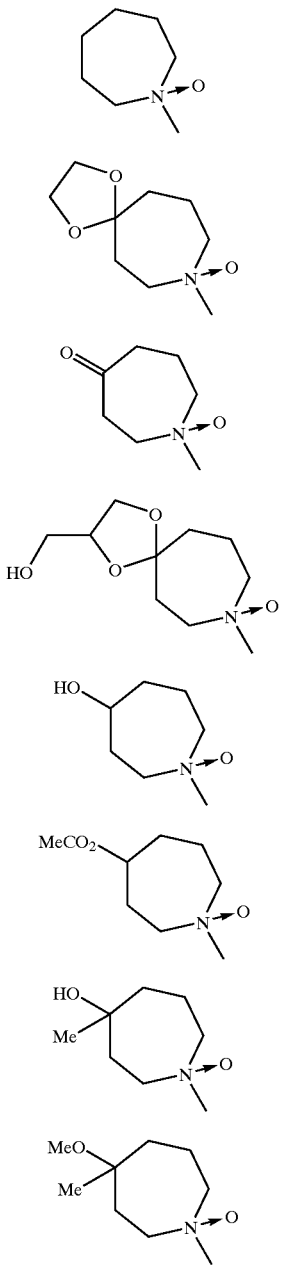
-continued
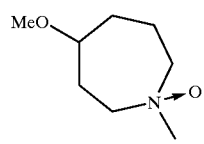  XVI-I
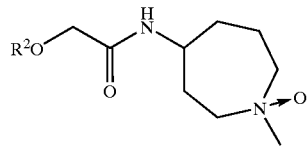  XVI-J
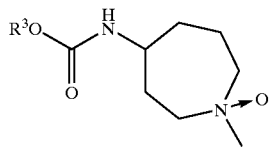  XVI-K
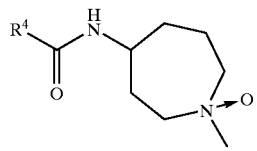  XVI-L
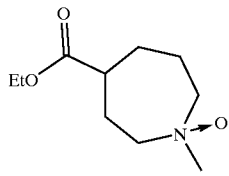  XVI-M
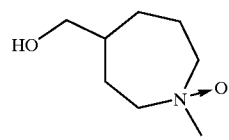  XVI-N
wherein X¹ and X² are independently
—H,
—F, or
—Cl;
wherein R¹ is
—CHO,
—COCH₃,
—COCHCl₂,
—COCHF₂,
—CO₂CH₃,
—SO₂CH₃, or
—COCH₂OH;
wherein R² is
—H,
—CH₃,
—CH₂Ph, or
—COCH₃;
wherein R³ is
—CH₃,
—CH₂CH₃,
—CH₂CH₂CH₃, or
-phenyl;

wherein R⁴ is
—H,
—CH₃,
—CH₂CH₃,
—CH₂CH₂CH₃,
—CH₂CH₂CH₂CH₃,
-phenyl,
—CH₂Cl,
—CHCl₂,
CH₂F,
—CHF₂,
-substituted aryl,
—CH₂—(aryl), or
-cycloalkyl (rings of 3–6 carbons).

CHART XVII - PIPERAZINES

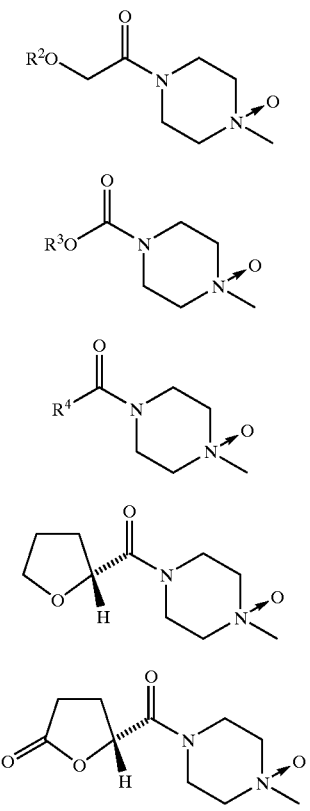

I wherein Q¹ is

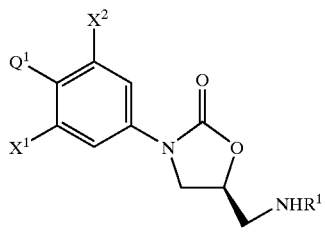  XVII-A

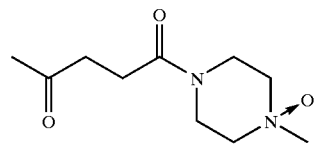  XVII-B

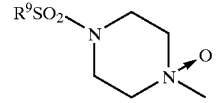  XVII-C

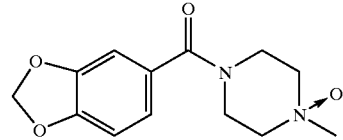  XVII-D

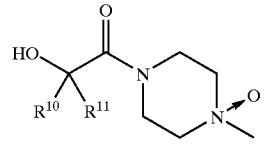  XVII-E

XVII-F

XVII-G

XVII-H

XVII-I

XVII-J wherein X¹ and X² are independently
—H,
—F, or
—Cl;
wherein R¹ is
—CHO,
—COCH₃,
—COCHCl₂,
—COCHF₂,
—CO₂CH₃,
—SO₂CH₃, or
—COCH₂OH;
wherein R² is
—H,
—CH₃,
—CH₂Ph, or
—COCH₃;
wherein R³ is
—CH₃,
—CH₂CH₃,
—CH₂CH₂CH₃, or
-phenyl;
wherein R⁴ is
—H,
—CH₃,
—CH₂CH₃,
—CH₂CH₂CH₃,
—CH₂CH₂CH₂CH₃,
-phenyl,
—CH₂Cl,
—CHCl₂, CH₂F,
—CHF₂,
-substituted aryl,
—CH₂—(aryl), or
-cycloalkyl (rings of 3–6 carbons);
wherein R⁹ is
—CH₃,
—CH₂Cl,
—CH₂CH=CH₂,
substituted aryl, or
—CH₂CN;
wherein R¹⁰ and R¹¹ are independently
—H,
—CH₃, or
-together form a cyclopropyl ring;
wherein R¹² is
—CH₂Ph, or
-substituted aryl.

CHART XVIII - PYRROLOPYRROLIDINES

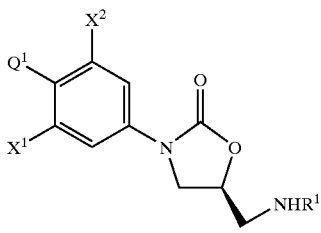

I wherein Q¹ is

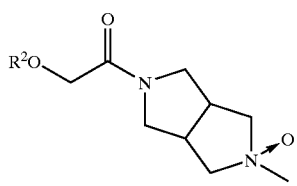

XVIII-A

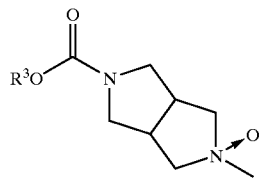

XVIII-B

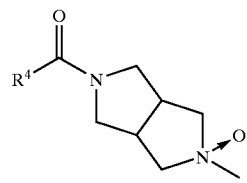

XVIII-C

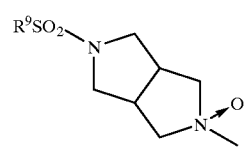

XVIII-D

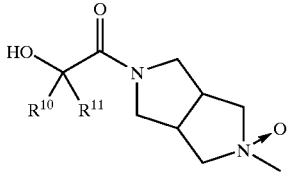

XVIII-E

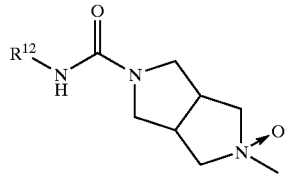

XVIII-F wherein X¹ and X² are independently
—H,
—F, or
—Cl;
wherein R¹ is
—CHO,
—COCH₃,
—COCHCl₂,
—COCHF₂,
—CO₂CH₃,
—SO₂CH₃, or
—COCH₂OH;
wherein R² is
—H,
—CH₃,
—CH₂Ph, or
—COCH₃;
wherein R³ is
—CH₃,
—CH₂CH₃,
—CH₂CH₂CH₃, or
-phenyl;
wherein R⁴ is
—H,
—CH₃,
—CH₂CH₃,
—CH₂CH₂CH₃,
—CH₂CH₂CH₂CH₃,
-phenyl,
—CH₂Cl,
—CHCl₂,
—CH₂F,
—CHF₂,
-substituted aryl,
—CH₂—(aryl), or
-cycloalkyl (rings of 3–6 carbons);
wherein R⁹ is
—CH₃,
—CH₂Cl,
—CH₂CH=CH₂,
substituted aryl, or
—CH₂CN;

wherein $R^{10}$ and $R^{11}$ are independently

—H,

—$CH_3$, or

-together form a cyclopropyl ring;

wherein $R^{12}$ is

—$CH_2Ph$, or

-substituted aryl.

What is claimed is:

1. A compound of the formula I

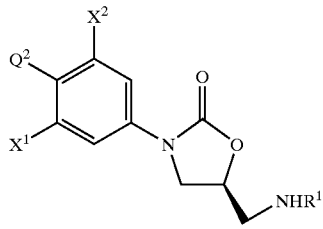

I wherein $X^1$ and $X^2$ are independently —H, —F, or —Cl;

$Q^1$ is:

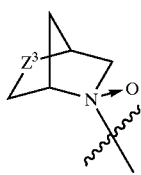

IV $Z^3$ is —$S(O)_2$—, or —O—; and $R^1$ is
  a) —CHO,
  b) —$COCH_3$,
  c) —$COCHCl_2$,
  d) —$COCHF_2$,
  e) —$CO_2CH_3$,
  f) —$SO_2CH_3$, or
  g) —$COCH_2OH$.

2. A compound of claim 1 wherein one of $X^1$ and $X^2$ is —H and the other is —F.

3. A compound of claim 1 wherein $X^1$ is —F and $X^2$ is —F.

4. The compound of claim 1 wherein $R^1$ is acetyl.

5. A compound of claim 1 which is:

4(S)-N-[[3-[3-fluoro-4-[(1S,4S)-2-thia-2,2-dioxo-5-azabicyclo[2.2.1]heptan-5-yl]phenyl]-2-oxo-5-oxazolidinyl]methyl]acetamide N-oxide; or 11(S)-N-[[3-[3-fluoro-4-[(1S,4S)-2-oxa-5-azabicyclo[2.2.1]heptan-5-yl]phenyl]-2-oxo-5-oxazolidinyl]methyl]acetamide N-oxide.

* * * * *